(12) United States Patent
Schmidt et al.

(10) Patent No.: US 10,136,898 B2
(45) Date of Patent: Nov. 27, 2018

(54) NARROW PROFILE SURGICAL LIGATION CLIP

(75) Inventors: Philip Schmidt, Rougemont, NC (US);
Dan Monahan, Raleigh, NC (US);
Brad Labarbera, Raleigh, NC (US);
Paul Whiting, Wake Forest, NC (US);
Steven Morris, Cary, NC (US);
Salvatore Castro, Raleigh, NC (US);
Michael Ramsey, Raleigh, NC (US);
Lynn Willett, Pittsboro, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 1203 days.

(21) Appl. No.: 13/616,120

(22) Filed: Sep. 14, 2012

(65) Prior Publication Data

US 2013/0245651 A1 Sep. 19, 2013

Related U.S. Application Data

(63) Continuation-in-part of application No. 13/042,864, filed on Mar. 8, 2011, now abandoned.
(Continued)

(51) Int. Cl.
*A61B 17/122* (2006.01)
*A61B 17/064* (2006.01)

(52) U.S. Cl.
CPC ........ *A61B 17/122* (2013.01); *A61B 17/0643* (2013.01); *A61B 17/1227* (2013.01)

(58) Field of Classification Search
CPC .... A61B 17/08; A61B 17/122; A61B 17/1227
(Continued)

(56) References Cited

U.S. PATENT DOCUMENTS

| 717,367 A | 12/1867 | Good |
| 125,311 A | 4/1872 | Lucas |

(Continued)

FOREIGN PATENT DOCUMENTS

| DE | 202010008714 | 12/2010 |
| EP | 0105414 | 4/1984 |

(Continued)

OTHER PUBLICATIONS

Chris H. Luebkeman and Donald Peting; Architectronics the Science of Architecture "What is a Moment?"; 1995; printed from: http://web.mit.edu/4.441/1_lectures/1_lecture5/1_lecture5.html.*

*Primary Examiner* — Vy Bui
(74) *Attorney, Agent, or Firm* — Baker Hostetler LLP

(57) ABSTRACT

A narrow profile surgical ligation clip has two legs with clamping surfaces joined by a hinge near the proximal ends, allowing the clip to reversibly open and close. A locking mechanism is proximal to the hinge to bias or lock the clip closed, including first and second jaw structures spaced on opposite sides of a longitudinal axis of the clip thereby defining a locking space therebetween. In one embodiment, a wedge or buttress body moves by application of an external force applied to a proximal end of the clip towards the hinge to move into the locking space such that one or more outer surfaces or projections of portions of the body fit into or abut against complementary surfaces or other parts of the locking mechanism or clip assembly to bias or lock the clip in a closed position and provide additional closing force to the inner clamping surfaces.

11 Claims, 22 Drawing Sheets

Related U.S. Application Data

(60) Provisional application No. 61/534,858, filed on Sep. 14, 2011, provisional application No. 61/312,156, filed on Mar. 9, 2010.

(58) Field of Classification Search
USPC .............. 606/120, 142, 143, 151, 157, 158
See application file for complete search history.

(56) References Cited

U.S. PATENT DOCUMENTS

| | | |
|---|---|---|
| 2,277,139 A | 3/1942 | Niemand |
| 2,931,086 A | 4/1960 | Rose |
| 2,968,041 A | 1/1961 | Skold |
| 3,274,658 A | 9/1966 | Pile |
| 3,279,479 A | 10/1966 | Solomon |
| 3,326,216 A | 6/1967 | Wood |
| 3,463,156 A | 8/1969 | Mcdermott et al. |
| 3,616,497 A | 11/1971 | Esposito, Jr. |
| 3,733,656 A * | 5/1973 | Stalder .......................... 24/557 |
| 3,827,438 A | 8/1974 | Kees, Jr. |
| 4,140,125 A | 2/1979 | Smith |
| 4,296,751 A | 10/1981 | Blake, III et al. |
| 4,337,774 A | 7/1982 | Perlin |
| 4,372,316 A | 2/1983 | Blake, III et al. |
| 4,414,721 A | 11/1983 | Hufnagel |
| 4,458,682 A | 7/1984 | Cerwin |
| 4,487,205 A | 12/1984 | Di Giovanni et al. |
| 4,493,495 A * | 1/1985 | Linn ............................. 281/45 |
| 4,514,885 A | 5/1985 | Delahousse et al. |
| 4,550,729 A | 11/1985 | Cerwin et al. |
| 4,579,118 A | 4/1986 | Failla |
| 4,586,501 A | 5/1986 | Claracq |
| 4,590,937 A | 5/1986 | Deniega |
| 4,638,804 A | 1/1987 | Jewusiak |
| 4,658,822 A | 4/1987 | Kees, Jr. |
| 4,660,558 A | 4/1987 | Kees, Jr. |
| 4,671,281 A | 6/1987 | Beroff et al. |
| 4,763,390 A * | 8/1988 | Rooz ............................. 24/487 |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,834,096 A | 5/1989 | Oh et al. |
| 4,835,824 A | 6/1989 | Durham et al. |
| 4,932,955 A | 6/1990 | Merz et al. |
| 4,942,886 A | 7/1990 | Timmons |
| 4,966,603 A | 10/1990 | Focelle et al. |
| 5,046,611 A | 9/1991 | Oh |
| 5,053,045 A | 10/1991 | Schmidt et al. |
| 5,062,846 A | 11/1991 | Oh et al. |
| 5,067,958 A | 11/1991 | Sandhaus |
| 5,074,870 A | 12/1991 | von Zeppelin |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,125,915 A | 6/1992 | Berry et al. |
| 5,171,247 A | 12/1992 | Hughett et al. |
| 5,171,249 A | 12/1992 | Stefanchik et al. |
| 5,201,416 A | 4/1993 | Taylor |
| 5,219,353 A | 6/1993 | Garvey, III et al. |
| 5,285,556 A | 2/1994 | Shorin et al. |
| 5,300,081 A | 4/1994 | Young et al. |
| 5,306,283 A | 4/1994 | Conners |
| 5,308,337 A | 5/1994 | Bingisser |
| 5,354,306 A | 10/1994 | Garvey, III et al. |
| 5,366,458 A | 11/1994 | Korthoff et al. |
| 5,366,459 A | 11/1994 | Yoon |
| 5,395,381 A | 3/1995 | Green et al. |
| 5,423,831 A | 6/1995 | Nates |
| 5,431,668 A | 7/1995 | Burbank, III et al. |
| 5,447,513 A | 9/1995 | Davison et al. |
| 5,462,558 A | 10/1995 | Kolesa et al. |
| 5,464,413 A | 11/1995 | Siska, Jr. et al. |
| 5,464,416 A | 11/1995 | Steckel |
| 5,474,567 A | 12/1995 | Stefanchik et al. |
| 5,474,569 A | 12/1995 | Zinreich et al. |
| 5,474,572 A | 12/1995 | Hayhurst |
| 5,509,920 A | 4/1996 | Phillips et al. |
| 5,527,318 A | 6/1996 | McGarry |
| 5,527,319 A | 6/1996 | Green et al. |
| 5,542,949 A | 8/1996 | Yoon |
| 5,575,802 A | 11/1996 | McQuilkin et al. |
| 5,591,178 A | 1/1997 | Green et al. |
| 5,593,414 A | 1/1997 | Shipp et al. |
| 5,601,573 A | 2/1997 | Fogelberg et al. |
| 5,601,574 A | 2/1997 | Stefanchik et al. |
| 5,626,592 A | 5/1997 | Phillips et al. |
| 5,632,753 A | 5/1997 | Loeser |
| 5,645,551 A | 7/1997 | Green et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,700,270 A | 12/1997 | Peyser et al. |
| 5,700,271 A | 12/1997 | Whitfield et al. |
| 5,713,912 A | 2/1998 | Porter |
| 5,720,756 A | 2/1998 | Green et al. |
| 5,725,537 A | 3/1998 | Green et al. |
| 5,725,538 A | 3/1998 | Green et al. |
| 5,732,921 A | 3/1998 | Lemire |
| 5,755,726 A | 5/1998 | Pratt et al. |
| 5,769,857 A | 6/1998 | Reztzov et al. |
| 5,779,718 A | 7/1998 | Green et al. |
| 5,810,853 A | 9/1998 | Yoon |
| 5,833,696 A | 11/1998 | Whitfield et al. |
| 5,843,097 A | 12/1998 | Mayenberger et al. |
| 5,843,101 A | 12/1998 | Fry |
| 5,858,018 A | 1/1999 | Shipp et al. |
| 5,908,430 A | 6/1999 | Appleby |
| 5,913,862 A | 6/1999 | Ramsey et al. |
| 5,921,991 A | 7/1999 | Whitehead et al. |
| 5,921,997 A | 7/1999 | Fogelberg et al. |
| 5,941,890 A | 8/1999 | Voegele et al. |
| 5,951,574 A | 9/1999 | Stefanchik et al. |
| 5,984,934 A | 11/1999 | Ashby et al. |
| 5,993,465 A | 11/1999 | Shipp et al. |
| 6,088,889 A | 7/2000 | Luther et al. |
| 6,179,850 B1 | 1/2001 | Goradia |
| 6,206,897 B1 | 3/2001 | Jamiolkowski et al. |
| 6,210,419 B1 | 4/2001 | Mayenberger et al. |
| 6,258,105 B1 | 7/2001 | Hart et al. |
| 6,261,303 B1 | 7/2001 | Mayenberger et al. |
| 6,273,253 B1 | 8/2001 | Forster et al. |
| 6,273,898 B1 | 8/2001 | Kienzle et al. |
| 6,277,131 B1 | 8/2001 | Kalikow |
| 6,290,575 B1 | 9/2001 | Shipp |
| 6,293,956 B1 | 9/2001 | Crainich et al. |
| 6,350,269 B1 | 2/2002 | Shipp et al. |
| 6,391,035 B1 | 5/2002 | Appleby et al. |
| 6,397,439 B1 * | 6/2002 | Langford ....................... 24/518 |
| 6,421,920 B1 | 7/2002 | Jensen |
| 6,464,710 B1 | 10/2002 | Foster |
| 6,599,298 B1 | 7/2003 | Forster et al. |
| 6,638,282 B2 | 10/2003 | Ramsey et al. |
| 6,652,545 B2 | 11/2003 | Shipp et al. |
| 6,699,258 B1 | 3/2004 | Sadler et al. |
| 6,716,226 B2 | 4/2004 | Sixto, Jr. et al. |
| 6,743,240 B2 | 6/2004 | Smith et al. |
| 6,746,461 B2 | 6/2004 | Fry |
| 6,776,783 B1 | 8/2004 | Frantzen et al. |
| 6,780,195 B2 | 8/2004 | Porat |
| 6,824,547 B2 | 11/2004 | Wilson, Jr. et al. |
| 6,824,548 B2 | 11/2004 | Smith et al. |
| 6,843,794 B2 | 1/2005 | Sixto, Jr. et al. |
| 6,863,675 B2 | 3/2005 | Wilson, Jr. |
| 6,880,699 B2 | 4/2005 | Gallagher |
| 6,911,033 B2 | 6/2005 | de Guillebon et al. |
| 7,001,412 B2 | 2/2006 | Gallagher et al. |
| 7,022,126 B2 | 4/2006 | De Canniere |
| 7,056,330 B2 | 6/2006 | Gayton |
| 7,070,602 B2 | 7/2006 | Smith et al. |
| 7,090,685 B2 | 8/2006 | Kortenbach et al. |
| 7,144,402 B2 | 12/2006 | Kuester, III |

(56) References Cited

U.S. PATENT DOCUMENTS

| | | |
|---|---|---|
| 7,175,648 B2 | 2/2007 | Nakao |
| 7,179,265 B2 | 2/2007 | Manetakis et al. |
| 7,182,775 B2 | 2/2007 | de Guillebon et al. |
| 7,207,997 B2 | 4/2007 | Shipp et al. |
| 7,223,272 B2 | 5/2007 | Francese et al. |
| 7,261,724 B2 | 8/2007 | Molitor et al. |
| 7,297,149 B2 | 11/2007 | Vitali et al. |
| 7,326,223 B2 | 2/2008 | Wilson, Jr. |
| 7,431,724 B2 | 10/2008 | Manetakis et al. |
| 7,572,266 B2 | 8/2009 | Young et al. |
| 7,582,095 B2 | 9/2009 | Shipp et al. |
| 7,615,058 B2 | 11/2009 | Sixto, Jr. et al. |
| 7,637,917 B2 | 12/2009 | Whitfield et al. |
| 7,678,125 B2 | 3/2010 | Shipp |
| 7,686,820 B2 | 3/2010 | Huitema et al. |
| 7,713,276 B2 | 5/2010 | Dennis |
| 7,717,926 B2 | 5/2010 | Whitfield et al. |
| 7,727,247 B2 | 6/2010 | Kimura et al. |
| 7,731,724 B2 | 6/2010 | Huitema et al. |
| 7,862,571 B2 | 1/2011 | Dennis |
| 2002/0111643 A1 | 8/2002 | Herrmann et al. |
| 2008/0027465 A1 | 1/2008 | Vitali et al. |
| 2009/0240266 A1 | 9/2009 | Dennis |
| 2010/0057104 A1 | 3/2010 | Sorrentino et al. |
| 2010/0249804 A1 | 9/2010 | Huitema |
| 2011/0087243 A1 | 4/2011 | Nguyen et al. |
| 2011/0224700 A1 | 9/2011 | Schmidt et al. |
| 2011/0288571 A1 | 11/2011 | Steinhilper et al. |
| 2011/0295291 A1 | 12/2011 | Trivisani |

FOREIGN PATENT DOCUMENTS

| | | |
|---|---|---|
| EP | 0 122 046 A1 | 10/1984 |
| FR | 1212165 | 3/1960 |
| FR | 1 356 257 A | 6/1964 |
| JP | 2010-172663 A | 8/2010 |
| SE | 2010848 | 2/2012 |
| WO | 2011 112577 A1 | 9/2011 |

\* cited by examiner

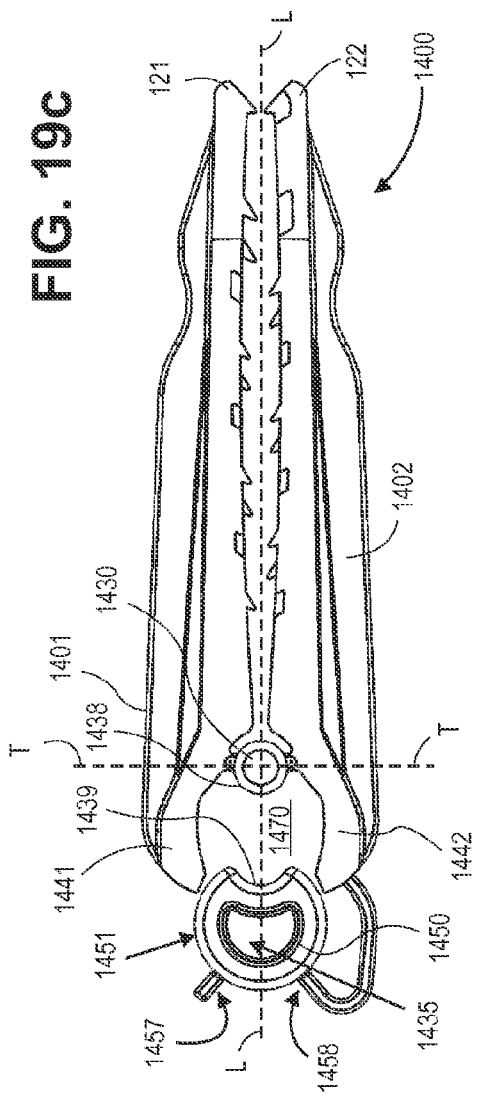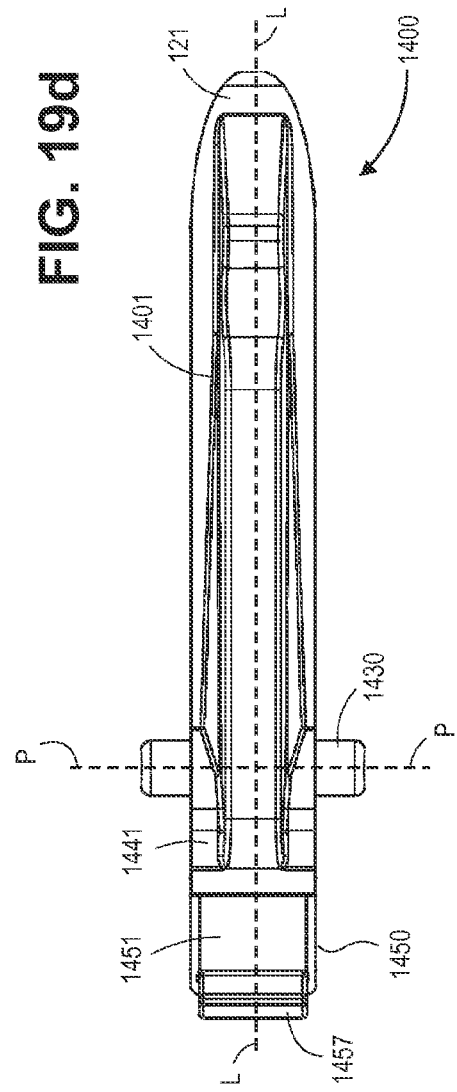

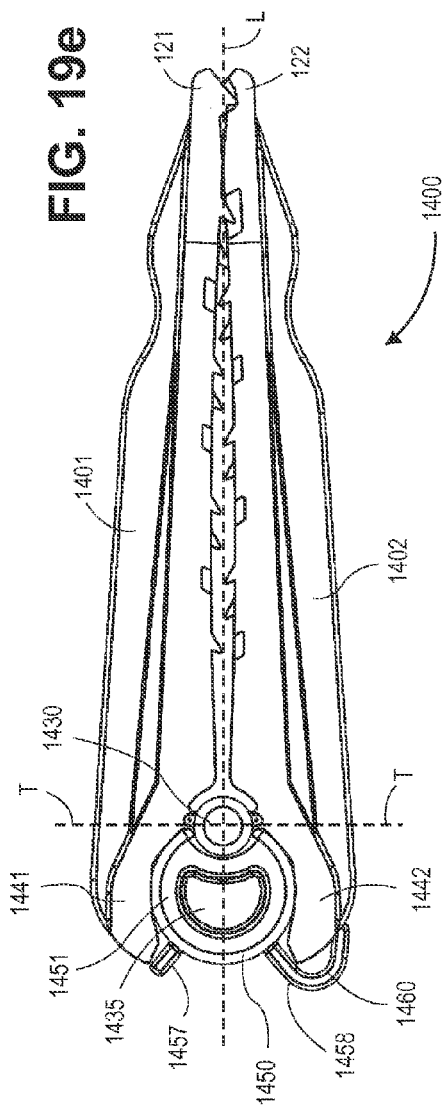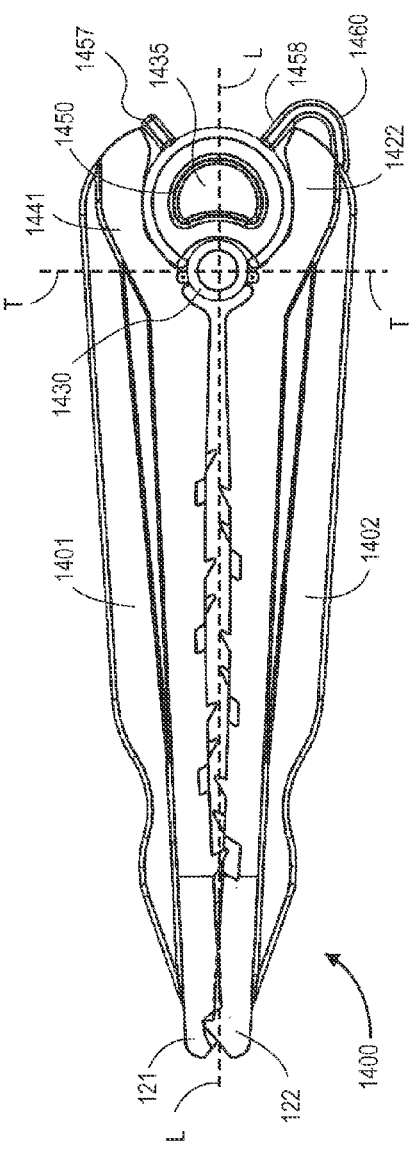

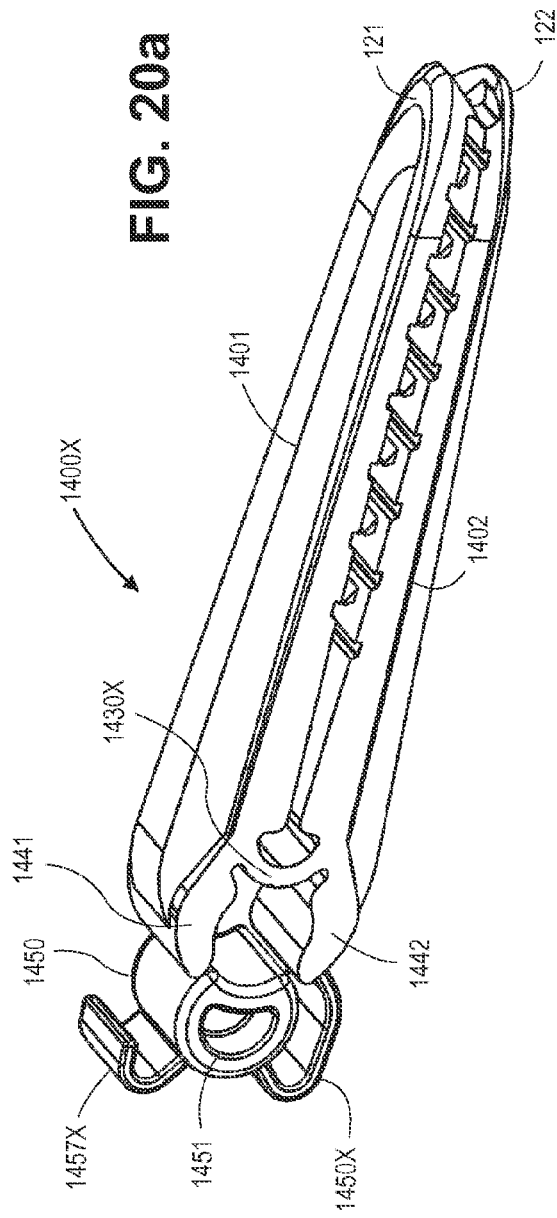
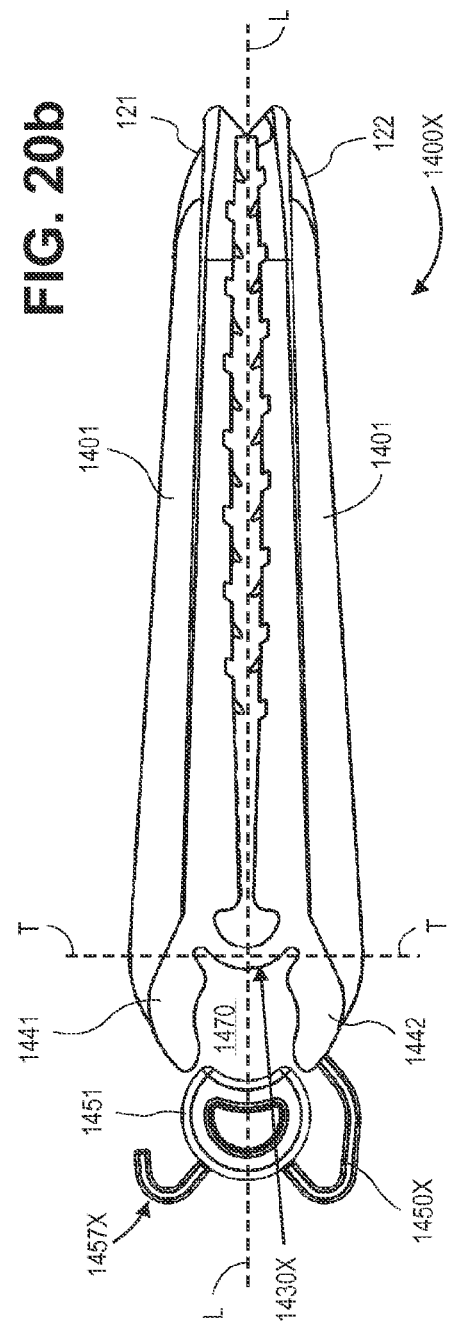

NARROW PROFILE SURGICAL LIGATION CLIP

CROSS-REFERENCE TO RELATED APPLICATIONS

This application claims priority to U.S. provisional patent application No. 61/534,858, filed on Sep. 14, 2011, and is a continuation-in-part and claims priority to U.S. patent application Ser. No. 13/042,864, filed Mar. 8, 2011, which claims priority to U.S. provisional patent application No. 61/312,156, filed on Mar. 9, 2010, the disclosures of all of which are incorporated by reference in their entireties.

FIELD OF THE INVENTION

The present invention relates to medical devices and in particular surgical clips for ligation of vessels or tissue.

BACKGROUND

Many surgical procedures require vessels or other fluid ducts or tissue conduits and structures to be ligated during the surgical process, such as, for example, veins or arteries in the human body. For example, many surgical procedures require cutting blood vessels, and these blood vessels may require ligation to reduce bleeding. In some instances, a surgeon may wish to ligate the vessel temporarily to reduce blood flow to the surgical site during the surgical procedure. In other instances a surgeon may wish to permanently ligate a vessel. Ligation of vessels or other tissues can be performed by closing the vessel with a ligating clip, or by suturing the vessel with surgical thread. The use of surgical thread for ligation requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. Accordingly, the use of ligating clips in endoscopic as well as open surgical procedures has grown dramatically.

Various types of hemostatic and aneurysm clips are used in surgery for ligating blood vessels or other tissues to stop the flow of blood. Such clips have also been used for interrupting or occluding ducts and vessels in particular surgeries such as sterilization procedures. Typically, a clip is applied to the vessel or other tissue by using a dedicated mechanical instrument commonly referred to as a surgical clip applier, ligating clip applier, or hemostatic clip applier. Generally, the clip is left in place after application to the tissue until hemostasis or occlusion occurs.

Ligating clips can be classified according to their geometric configuration (e.g., symmetric clips or asymmetric clips), and according to the material from which they are manufactured (e.g., metal clips or polymeric clips). Symmetric clips are generally "U" or "V" shaped and thus are substantially symmetrical about a central, longitudinal axis extending between the legs of the clip. Symmetric clips are usually constructed from metals such as stainless steel, titanium, tantalum, or alloys thereof. But, with the advent of high technology diagnostic techniques using computer tomography (CATSCAN) and magnetic resonance imaging (MRI), metallic clips have been found to interfere with the imaging techniques. To overcome such interference limitations, biocompatible polymers have been increasingly used for surgical clips.

Some well known polymeric clips are disclosed in U.S. Pat. No. 4,834,096 and U.S. Pat. No. 5,062,846. These plastic clips generally comprise a pair of curved legs joined at their proximal ends with an integral hinge or heel, and a closure or locking mechanism at their distal ends. Another example of a bio-compatible clip is shown in U.S. Pat. No. 4,671,281, which includes a mechanism to be actuated on a proximal end of the clip for causing the distally extending legs of the clip to converge. However this clip is: (i) rudimentary in construction, (ii) does not provide adequate clip closing or clamping strength, (iii) lacks any complex geometry which would adequately retain the clip in a closed position, and further (iv) is too unstable when closed to be safely applied over vessels. Examples of metal hemostatic clips are shown in U.S. Pat. No. 3,326,216 and U.S. Pat. No. 5,908,430.

In all of the known ligating clips however, there remains a need to improve the effectiveness of clamping about a vessel, while minimizing the damage to the vessel and surrounding tissue. For endoscopic surgical procedures, it is important is use tools and instruments that have the smallest, narrowest profile possible, such as the shafts of a tubular endoscope. Prior art polymeric and metal clips do not lend themselves to deployment through small diameter instrumentation, such as, for example, a ~5 mm endoscope. Known prior art clips can be very wide profile, especially when in the open position prior to closure and ligation, and thus require larger, wider endoscopic instruments and appliers for use in surgery. It is desirable therefore to provide for a surgical ligation clip that has the narrowest profile possible. It may also be desirable to allow for a clip to be opened again after initial closure, which is especially a problem with known surgical clips, such as metal hemostatic clips. Furthermore, prior art polymeric clips involve locking the distal ends of their legs together in order to clamp down on the vessel or structure being ligated. Such closure of a clip having locking parts at its distal end generally causes or requires dissection, removal, or clearance of additional surrounding tissue, in order to allow the clip's locking features to come together, and/or due to actuation of an applier tool surrounding or applied against the distal clip ends, requiring additional time during a surgical procedure and damage to tissue. In other cases, the user may choose not to prepare a path for the locking features and rely on the locking features penetrating through the tissue. In these cases, the locking feature may have difficulty penetrating the tissue or may have difficulty locking after it has penetrated the tissue. This technique may also result in unintended penetration of tissue or vessels.

Therefore it is desirable to provide a clip which minimizes such dissection of tissue during application. It is further desirable to provide a clip which provides a proper, well-calibrated, reliable clamping force, such that the clip when closed is stable around the vessel ligated.

Accordingly, there is a need to provide an improved surgical ligating clip that serves to reliably secure the tissue or vessel engaged by the clip, while robustly remaining attached to the vessel with a minimum level of damage to tissue.

SUMMARY OF THE INVENTION

The invention provides, in one or more embodiments, a narrow profile surgical ligation clip which has two legs with clamping surfaces joined by a main clip hinge near the proximal end portion of the clip, allowing the clip to reversibly open and close. One or more embodiments of the surgical clip include a proximal locking mechanism to bias or lock the clip closed, which can be actuated while the legs of the clip are closed. The ligation clip of the present invention can therefore be locked proximally while also being fed through an applier in a closed or semi-closed position. The locking mechanism can include first and second jaw structures extending proximally from the hinge area and spaced on opposite transverse sides of a longitudinal axis of the clip thereby defining a locking space therebetween. In one embodiment, a wedge or buttress body moves by application of an external force applied to a proximal end of the clip to move said body into the locking space such that one or more outer surfaces or portions of the body fit into or abut against complementary surfaces or other parts of the locking mechanism and/or clip to bias or lock the clip in a closed position and provide additional closing force to the inner clamping surfaces, as well as to stabilize the locked, closed configuration of the clip.

In a first embodiment of the invention, a surgical ligation clip, defining a longitudinal axis, comprises first and second legs each extending along the longitudinal axis and having proximal and distal end portions with respect to said longitudinal axis. A clip hinge joins the first and second legs at a point on their respective proximal end portions, the first and second legs each having inner clamping surfaces between the clip hinge and the distal end portions of said first and second legs, the clamping surfaces being substantially apposed when the clip is in a fully closed position. A first jaw structure on the first leg extends proximal to the clip hinge, the first jaw structure having a first curved inner surface extending from the clip hinge and facing the longitudinal axis and being substantially concave viewed from said axis. A second jaw structure on the second leg extends proximal to the clip hinge and has a second curved inner surface extending from the clip hinge and facing the longitudinal axis and being substantially concave viewed from said axis. A buttress body extends from and is connected to at least one of the first or the second jaw structures by at least a first living hinge extending from said first or second jaw structure, the buttress body having an outer surface. The first and second jaw structures are spaced from the longitudinal axis on opposite sides thereof and define a locking space therebetween, the buttress body being moveable into the locking space such that at least first and second curved planar segment abutment portions of the outer surface of the buttress body each abuts against the substantially concave curved inner surfaces of the first and second jaw structures to bias the clip in a closed position.

The invention further includes one or more methods of applying any of the clips disclosed herein over a vessel during surgery, including opening the clip legs and positioning the clip about a vessel, and then closing the clip legs on the vessel to occlude the vessel, and finally actuating a buttress body on the clip to move into a locking space defined at the proximal end portion of the clip to urge the clip legs to clamp and remain closed over the vessel and to prevent such legs from separating, thereby rendering the clip locked over the vessel.

There has thus been outlined, rather broadly, certain embodiments of the invention in order that the detailed description thereof herein may be better understood, and in order that the present contribution to the art may be better appreciated. There are additional embodiments and features of the invention that will be described below.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

BRIEF DESCRIPTION OF THE DRAWINGS

FIG. 12 is a perspective view from the top of the clip shown in FIG. 11a;

FIG. 13 is a side view of the clip shown in FIG. 11a;

FIG. 19c is a side view of the surgical ligation clip of FIG. 19a, with the clip legs substantially closed;

FIG. 19*d* is a top view of the surgical ligation clip of FIG. 19*a*;

FIG. 19*e* is a side view of the surgical ligation clip of FIG. 19*a*, with the clip legs fully closed and the clip in a locked position;

FIG. 19*f* is another side view of the surgical ligation clip of FIG. 19*e*, with the clip legs fully closed and the clip in a locked position;

FIG. 20*a* is a view of a surgical ligation clip according to another embodiment of the invention;

FIG. 20*b* is a side view of the surgical ligation clip of FIG. 20*a*, with the clip legs substantially closed.

DETAILED DESCRIPTION

Figure 1:
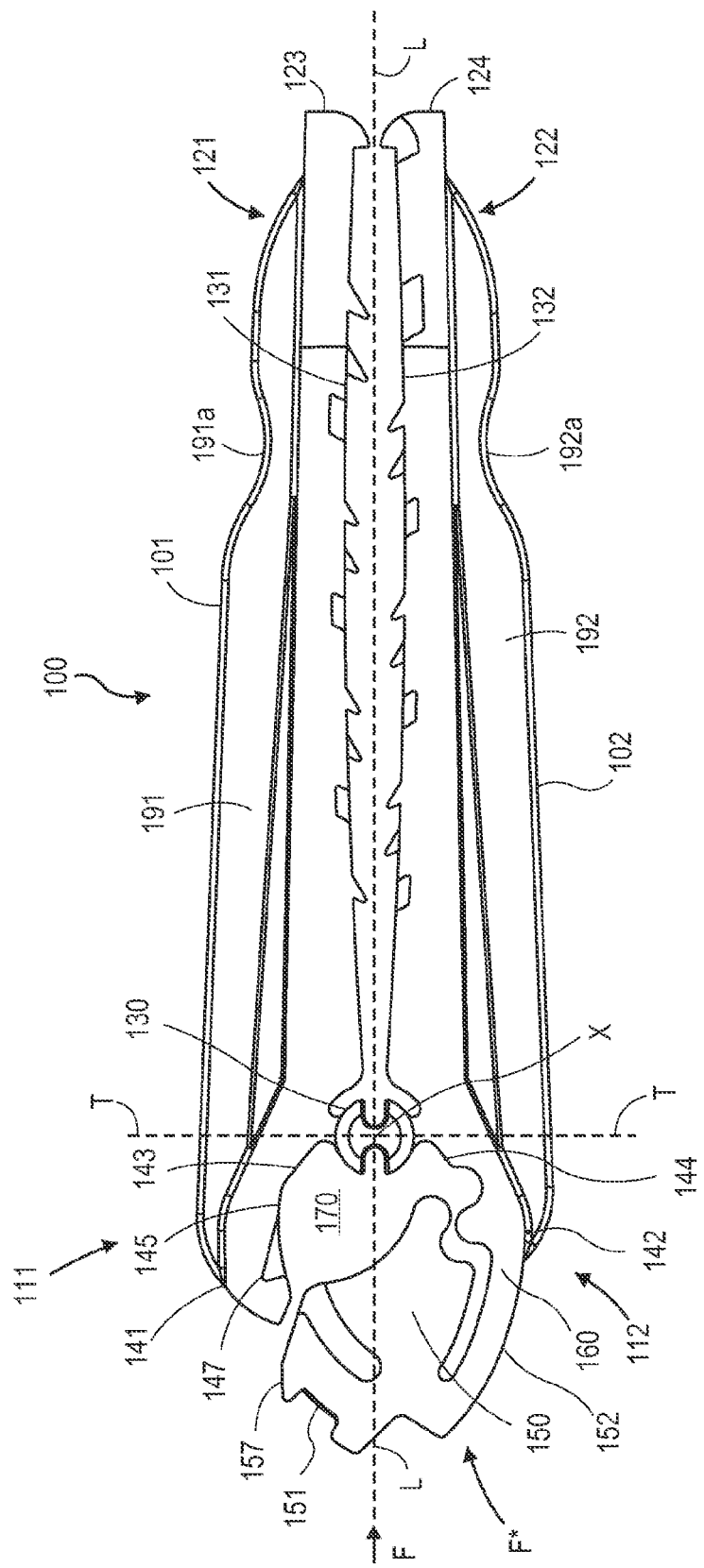
FIG. 1 shows a view of a first embodiment of a surgical ligation clip of the present invention.

The invention will now be described with reference to the drawing figures, in which like parts are referred to with like reference numerals throughout.

FIG. 1 shows a view of a first embodiment of a surgical ligation clip 100 of the present invention. The clip 100 defines a longitudinal axis "L" along its longest dimension and includes a first leg 101 and a second leg 102 each extending along the longitudinal axis L and having proximal 111, 112 and distal 121, 122 end portions with respect to said longitudinal axis. As used throughout herein, the term "proximal" shall refer to the portion of the clips referenced herein which is away from the tips of the clip which open, and "distal" shall refer to the portion of the clip at the tips which open, in accordance with the convention that the clip is inserted distal tip first through an instrument towards an anatomical body to be ligated, such that distal generally refers to the direction away from the user or applier of the surgical clip and proximal refers to the direction opposite to distal.

In clip 100, a clip hinge 130 joins the first and second legs 101, 102 at a point on their respective proximal end portions 111, 112, the first and second legs each having respective inner clamping surfaces 131, 132 between the clip hinge 130 and the distal ends 123, 124 of said first and second legs, the clamping surfaces being apposed when the clip is in a fully closed position. As used herein, the term "apposed" when used with regard to the inner clamping surfaces 131, 132 shall mean close to, or nearly in contact with each other, allowing for some small spacing therebetween or a concave radius of curvature for the clamping surfaces, such to allow for a clipped vessel to reside between such apposed surfaces. The clip hinge 130 can include a trunnion-like bar or cylindrically shaped body or tube which defines a lateral pivot axis "P" (shown in FIGS. 2*b* and 2*c*) about which the legs 101 and 102 pivot as the clip moves from open to closed position and vice versa. A first jaw structure 141 on the first leg 101 extends proximal to a transverse axis "T" which is perpendicular to both the longitudinal axis L and lateral pivot axis P, all intersecting at a point "X" centered on the clip hinge 130, as shown in FIG. 1.

As used throughout herein, the term "lateral" shall directionally mean orthogonal to both the directions of the longitudinal axis L and transverse axis T, and parallel to pivot axis P as shown in the figures, while the term "longitudinal" shall refer to the direction and axis along which the longest dimension of the clip is oriented, generally being the central axis along which the clip legs extend from their proximal ends through the hinge point to their distal ends; the term "transverse" shall refer to the direction which is orthogonal to the longitudinal direction in the plane which spans the range of movement when the clip legs open and close.

The first jaw structure 141 includes a first curved inner surface 143 extending from the clip hinge 130, the first curved inner surface 143 having a complex surface which is oriented at changing angles with respect to, but is generally facing towards, the longitudinal axis L, as shown in FIG. 1. The curved inner surface 143 is therefore substantially concave when viewed from the longitudinal axis (or plane spanning the longitudinal axis and pivot axis). As used herein, the term "substantially concave" shall mean a surface which is concave in overall curvature, but which may include one or more component areas which may have convex segments or protrusions, such as a notch surface or recess for mating thereto. A second jaw structure 142 is on the second leg 102 extending proximal to the transverse axis T and has a second curved inner surface 144 extending from the clip hinge 130. As used herein, the "curved inner surface" can include either a single smoothly curved surface segment, or a series of connected curved or straight planar segments, which, taken together, form an overall generally curving surface. As described herein, the surgical clip of the present invention provides that the jaws 141 and 142 are each substantially proximal to a transverse plane extending through transverse axis T and lateral pivot axis P, thus behind or proximal to the clip hinge 130, thereby providing a means for actuating the clip legs 101 and 102 and biasing or locking the clip and its mating faces 131, 132 in a closed position, which biasing or locking means can be actuated and/or applied by acting substantially only on the proximal end portions of the clip 100, without having to lock the distal ends 123, 124 to each other or use a clip applier tool which acts on said distal ends 123, 124, thereby obviating the need to dissect tissue around the distal end of the clip.

As shown in FIG. 1, the means for biasing or locking the clip closed includes a wedge or buttress body 150 which extends from and is connected to the second jaw structure 142 by a first living hinge 160 at a proximal end of said second jaw structure 142, the buttress body 150 having an outer surface 151 at a proximal first end portion thereof, which is also disposed approximately as the proximal end of the clip 100 overall. The first and second jaw structures 141, 142 are spaced on opposite sides of the longitudinal axis L and define a locking space 170 therebetween. The wedge or buttress body 150 is pivotable about the living hinge 160 to move into the locking space 170 such that the outer surface 151 of the proximal first end portion of the buttress body 150 abuts against a proximal portion 145 of the curved inner surface 143 of the first jaw structure 141 to bias the clip in a closed position (as best shown in FIGS. 11*a*, and 12-14). Although the clip 100 is shown in FIG. 1 in a closed position, this is with the locking means of the first and second jaws 141, 142 and buttress body 150 being in the "unlocked" position as shown in FIGS. 1, 2*a*, and 3-7. Once the buttress body is in the "locked" position as shown in FIGS. 11*a* and 12-14, the first and second jaws 141, 142 are urged or spread apart (shown, as an example, by arrows "J1" and "J2" in FIGS. 13*a* and 14*a*) by action of surfaces of the wedge/buttress body 150 acting on portions of curved inner surfaces 143, 144, which act as moments about the clip hinge 130 and lateral pivot axis P to urge the legs 101, 102 and its inner clamping surfaces 131, 132 to become more closely apposed to each other, thereby providing additional clamping and closing force over a vessel around which the clip is applied.

A variety of means may be used to actuate the wedge or buttress body 150 from the unlocked position in FIG. 1 to the locked position shown in FIGS. 11*a*, 12-14. As shown in FIG. 1, an external force, shown, for example, as arrow "F"

in FIG. 1, may be applied to a proximal end of the pivoting buttress body 150, in this example the external force F being substantially aligned with the longitudinal axis L. Alternatively, the external force applied may be at a small angle to the longitudinal axis L, such as, for example, a force shown by arrow "F*" shown in FIG. 1. In either case, the applied external force will create a moment about living hinge 160 to pivot the buttress body 150 into the locking space 170. The external force may be applied by an actuating rod or other structural means in an applier instrument, or may be another clip as fed through a multi-clip applier. As one example, the clip 100 may be inserted through an instrument having a bore or channel for receiving the clip 100, through which the clip 100 may travel distally for positioning near a vessel during a surgical procedure. The clip may be inserted in a legs closed position, but with the proximal locking means including buttress body 150 in open, unlocked position. Because the clip 100 can be inserted in such fashion in closed form, the clip forms a narrow profile and can fit in smaller sized surgical instruments, thereby allowing for smaller incisions and tissue dissection or damage during surgery. A rod or other actuating mechanism translating or moveable on the instrument inserting the clip, or a second instrument or second clip used in conjunction with the instrument used for inserting and positioning the clip in place, maybe used to lock the clip by application of an external force on the proximal end portion of the clip as discussed above.

Thus, a method of applying a surgical ligation clip on a vessel in accordance with an embodiment of the invention includes positioning a clip, such as, for example, clip 100, in an open position proximate a vessel, the clip having first and second legs each extending along a longitudinal axis of the clip and having proximal and distal end portions with respect to said longitudinal axis, a clip hinge means joining the first and second legs at a point on their respective proximal end portions, the first and second legs each having inner clamping surface means between the clip hinge and the distal end portions of said first and second legs, the clamping surface means being apposed when the clip is in a fully closed position. A locking means for biasing the legs closed may extend proximal to a transverse axis perpendicular to the longitudinal axis intersecting at a point centered on the clip hinge. The method includes applying an external force to a proximal end portion of the clip or of one of the legs which forms a portion of the locking means, to move a body formed as a first part of said locking means from a first position to a second position to provide an abutment force between said body and a surface formed on a second part of said locking means to bias the clip in a closed position. In the method, an instrument may be used, wherein, in moving the clip through the instrument prior to positioning the clip proximate a vessel, a portion of the instrument, or another clip moving through the instrument, opens the clip from a closed position to an open position, such that the legs of the clip open for placement of the clip around a vessel. The locking means may then be applied to the proximal end portion of the clip to move and bias the legs closed and clamp the clip more fully over the vessel.

In FIG. 1, the clamping surfaces appear substantially parallel to each other, oriented, in the clip closed position, substantially or very close to parallel to a plane extending through the longitudinal axis L and lateral pivot axis P. However, in an embodiment of the invention, the inner clamping surfaces 131, 132 may be slightly curved concave when facing said surfaces, such that the surfaces bow away from the longitudinal axis L and straighten slightly when clamping force is applied by action of the locking mechanism of the buttress body 150 acting against jaws 141, 142. This allows for enhanced grasping and occlusion of vessels around which the clip 100 is applied, wherein the clamping force is spread more evenly across the clamping surface.

The living hinge 160 connecting the wedge or buttress body 150 to the second jaw 142 can be integral to the second jaw 142 such that the clip body of second leg 102 proximal to transverse axis T extends as a single unitary structure including the second jaw 142 and entire wedge or buttress body 150. Accordingly, in the wedge or buttress body 150, a lateral beam or curved body 152 connects the living hinge 160 to the rest of the buttress body 150, which beam 152 curves from the living hinge 160 (which is separated by a distance from the longitudinal axis L) towards the longitudinal axis L. As shown in FIG. 1 portions of wedge of buttress body 150 can be oriented on both sides of longitudinal axis L. The pivot axis of living hinge 160 extends in a lateral direction parallel the lateral pivot axis P of the main clip hinge 130.

Figure 12:
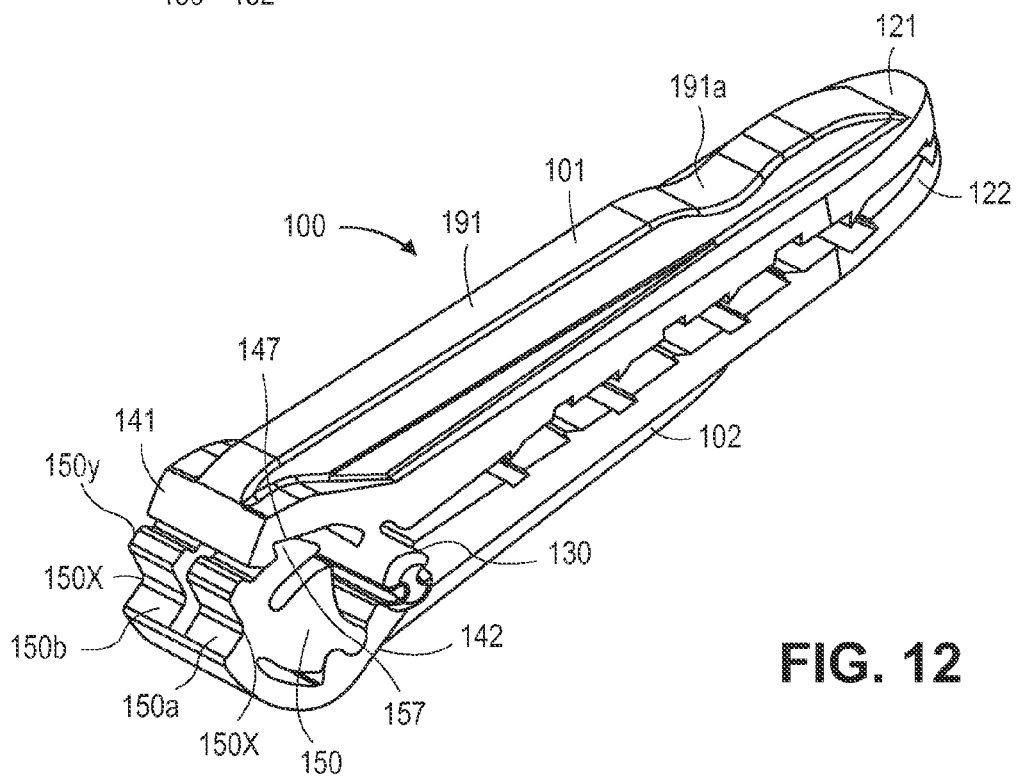
Figure 4:
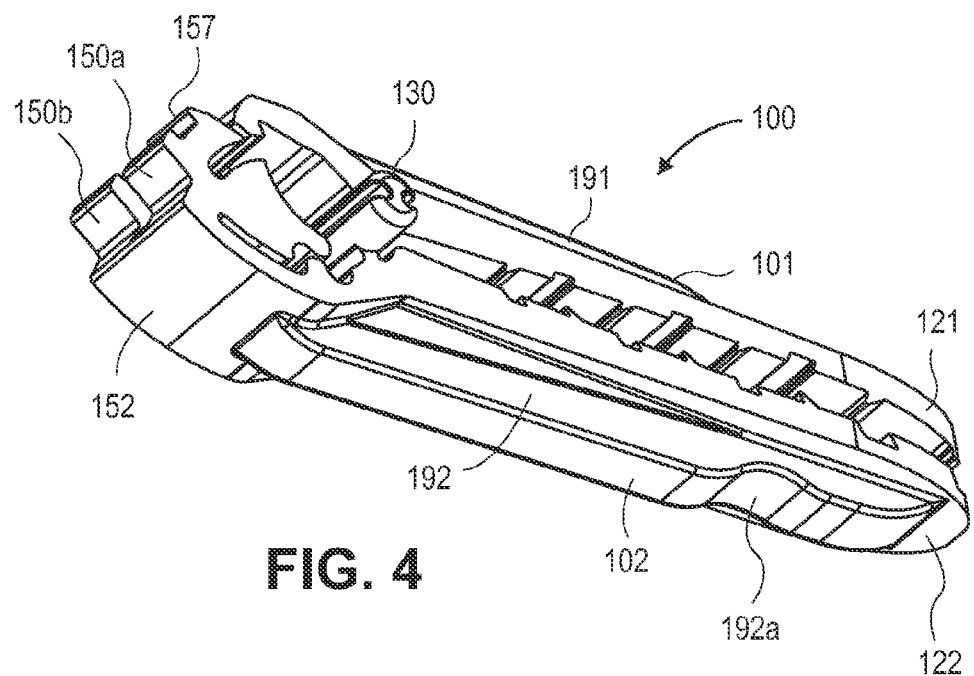
Figure 11C:
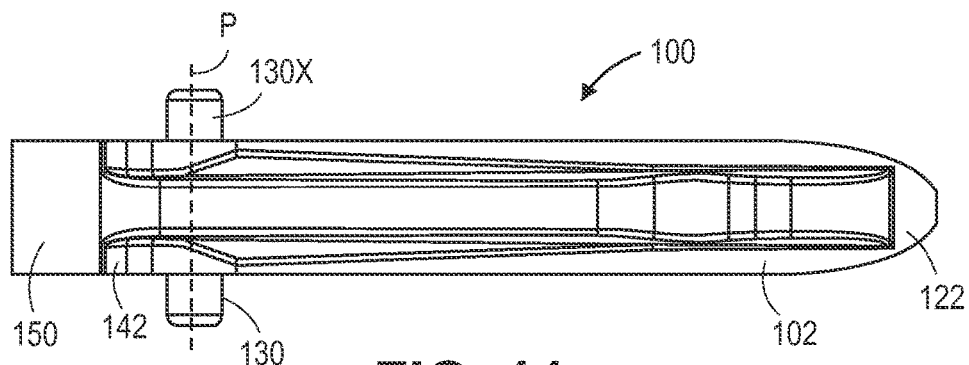
FIGS. 11a, 11b, and 11c show side, top, and bottom views respectively, of the clip shown in FIG. 1, with the proximal locking components in locked position.
Figure 11A:
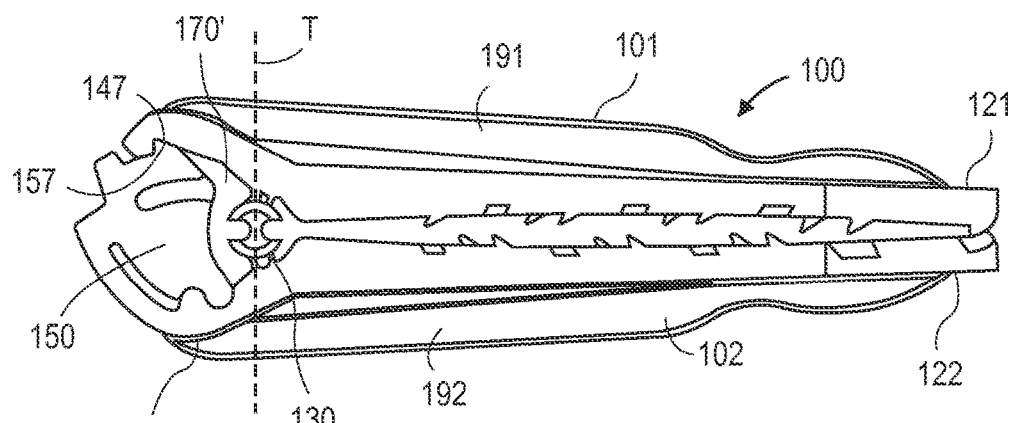
Figure 11B:
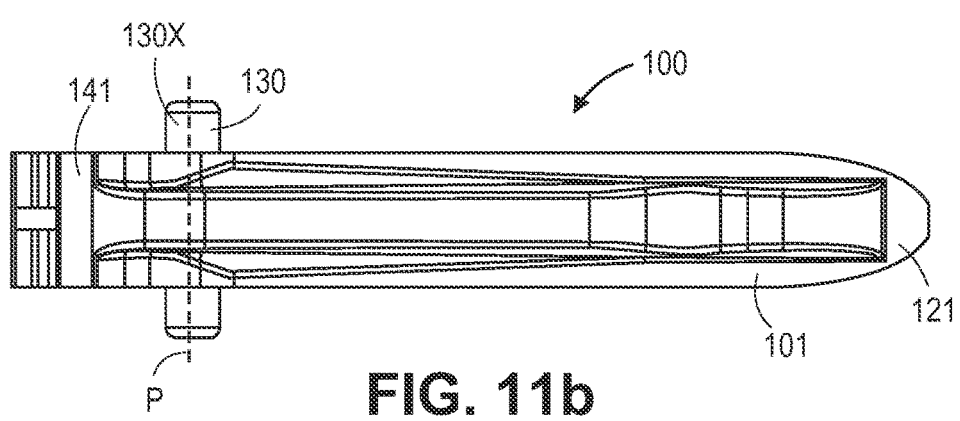
Figure 14A:
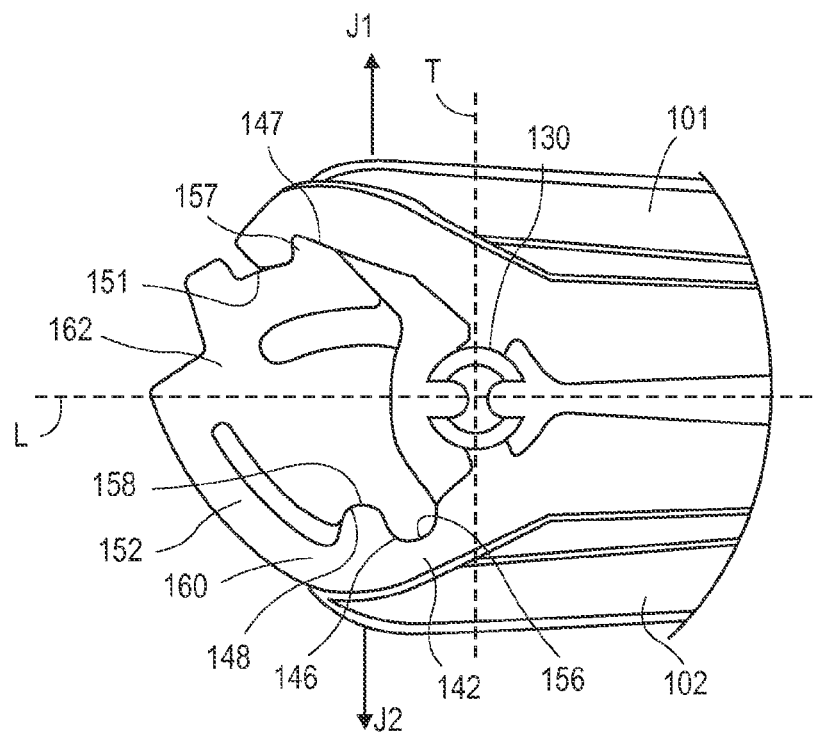
FIG. 14a is a close-up detail view of the portion of the clip shown in FIG. 14 in region "A4" therein.
Figure 14:
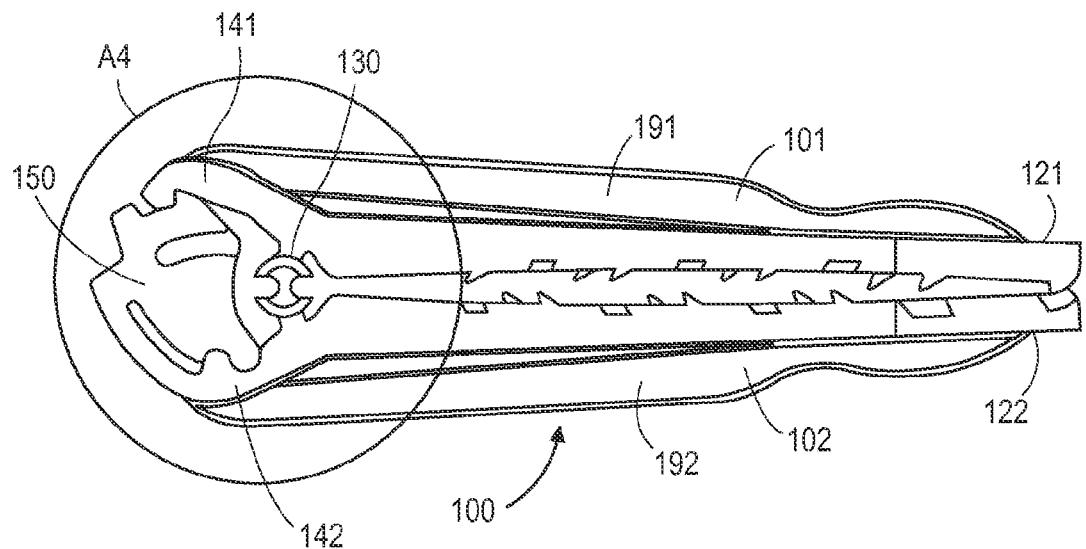
FIG. 14 is a side view of the clip shown in FIG. 11a from the side opposite to that shown in FIG. 13.

The clip 100 provides a locking mechanism cooperating between the buttress body 150 and another portion of the clip. In the clip 100 shown in FIG. 1, the proximal end portion 145 of the curved inner surface 143 of the first jaw structure 141 defines a notch 147 recessed from said curved inner surface 143, and the buttress body 150 defines a detent 157 formed on the outer surface thereof, the detent 157 mating with the notch 147 when the buttress body 150 is pivoted into the locking space 170 to bias the clip in the closed position, as best shown in FIGS. 11a, 12, and 14.

Figure 2A:
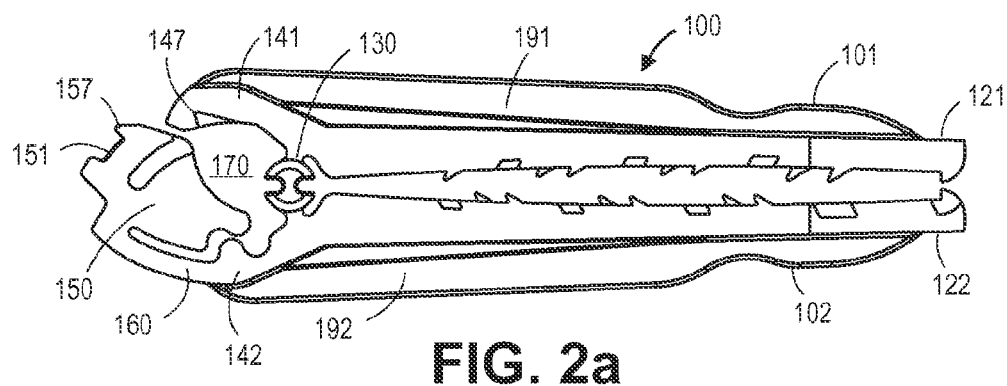
FIGS. 2a, 2b, and 2c show side, top, and bottom views respectively, of the clip shown in FIG. 1.
Figure 2B:
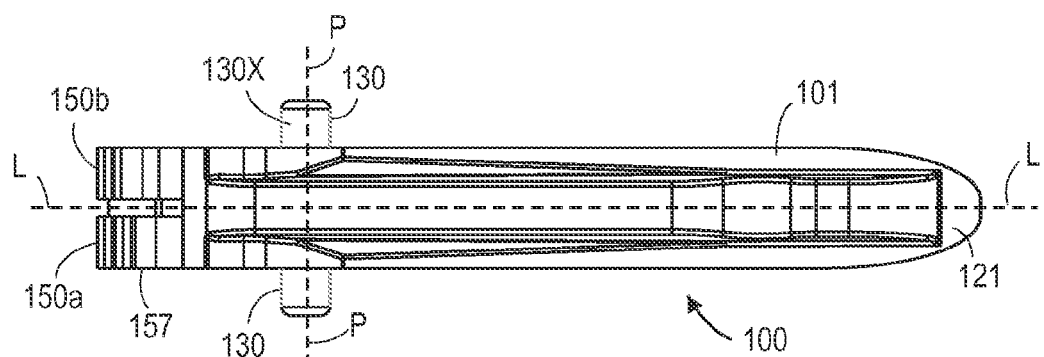
Figure 2C:
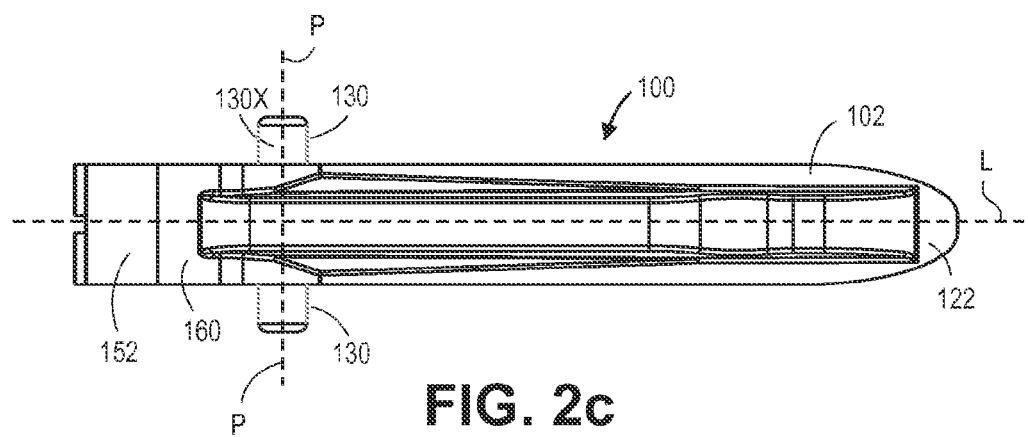
Figure 3:
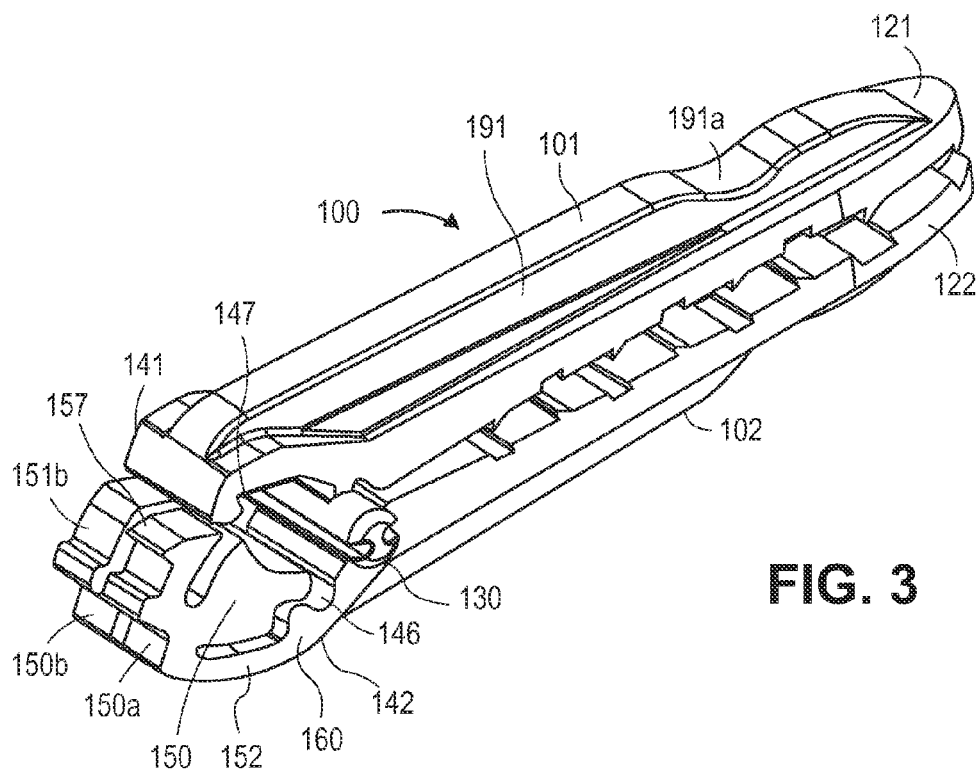
FIGS. 3 and 4 show perspective views of the clip shown in FIG. 1 from a first side.
Figure 7B:
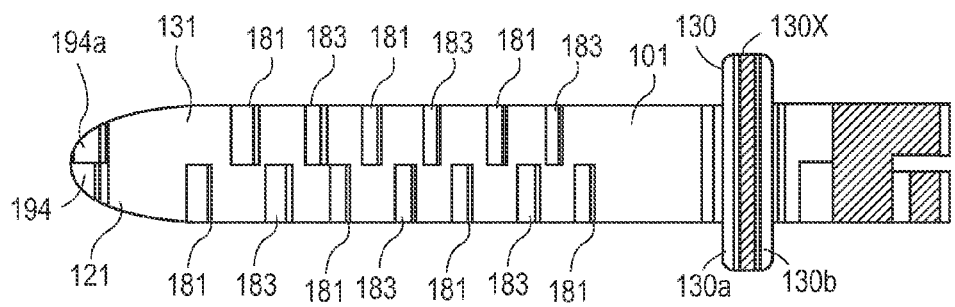
FIG. 7b is a sectional view of the clip shown in FIG. 7 taken along section C-C in the direction shown in FIG. 7.
Figure 7:
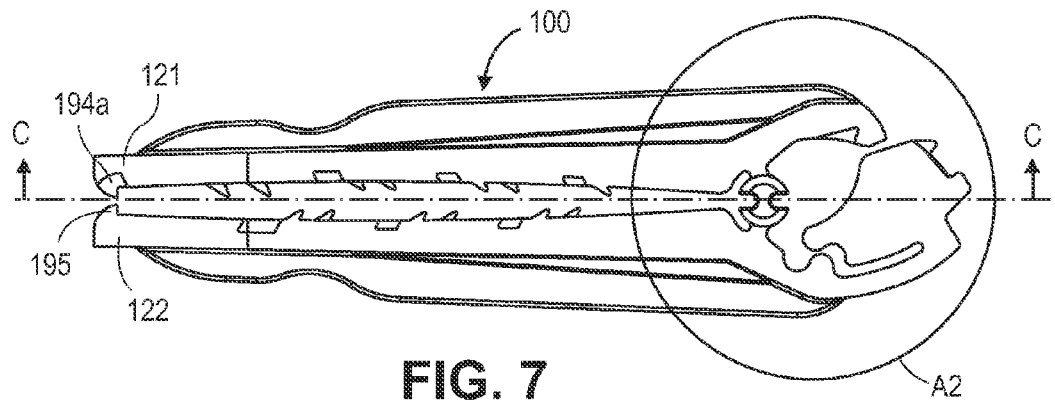
FIG. 7 is another side view of the clip shown in FIG. 1 from the opposite side to that shown in FIG. 6.
Figure 7A:
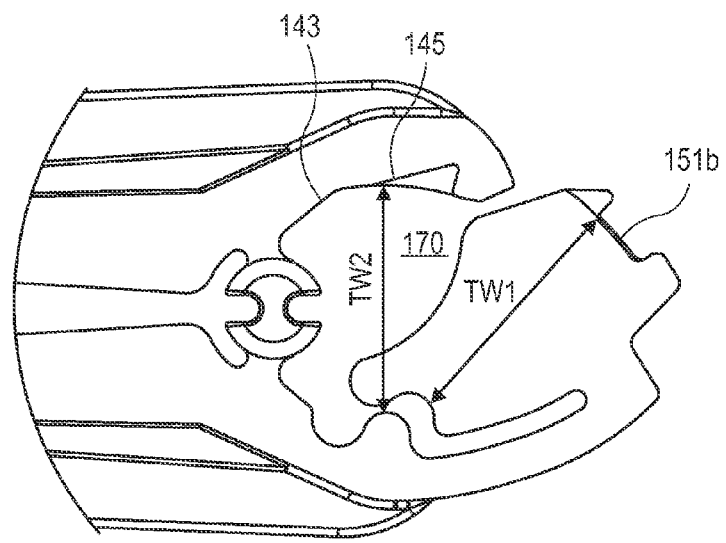
FIG. 7a is a close-up detail view of the portion of the clip shown in FIG. 7 in region "A2" therein.
Figure 8A:
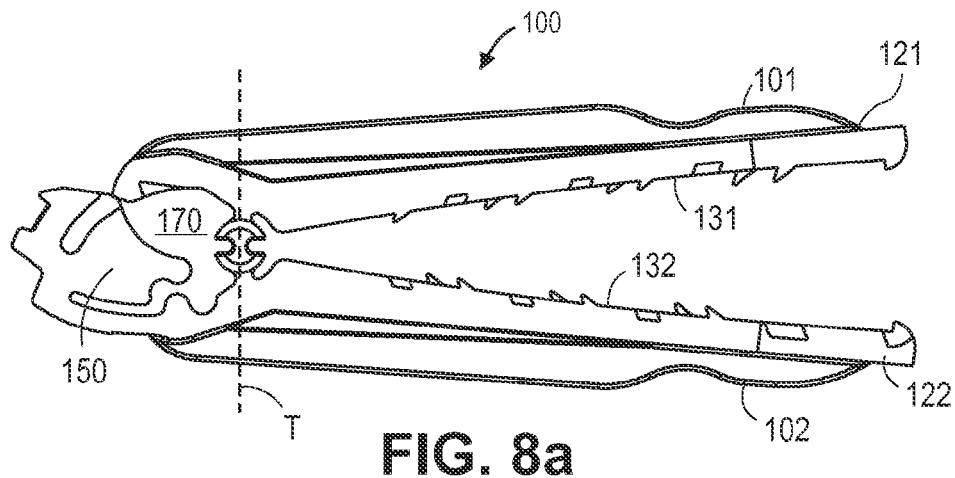
FIGS. 8a, 8b, and 8c, are side, top, and bottom views, respectively, of the clip shown in FIG. 1 in an open position.
Figure 8B:
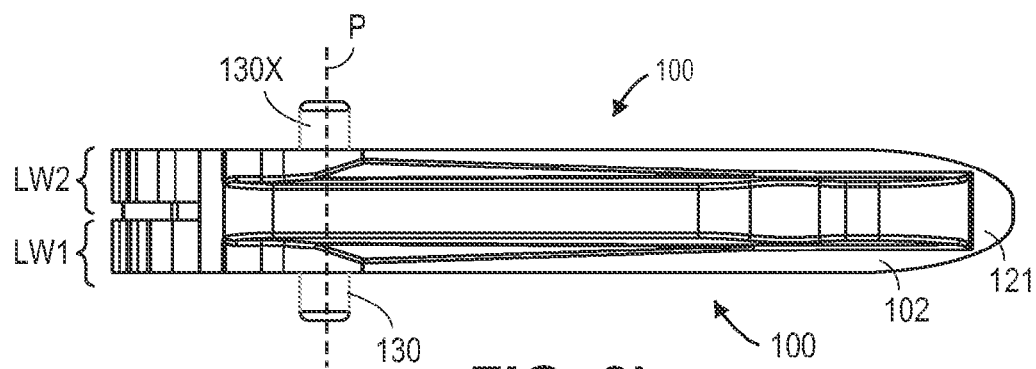
Figure 8C:
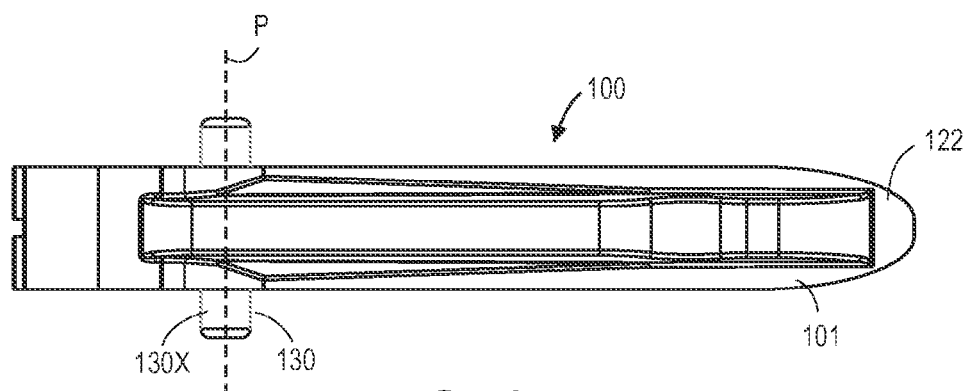
Figure 9:
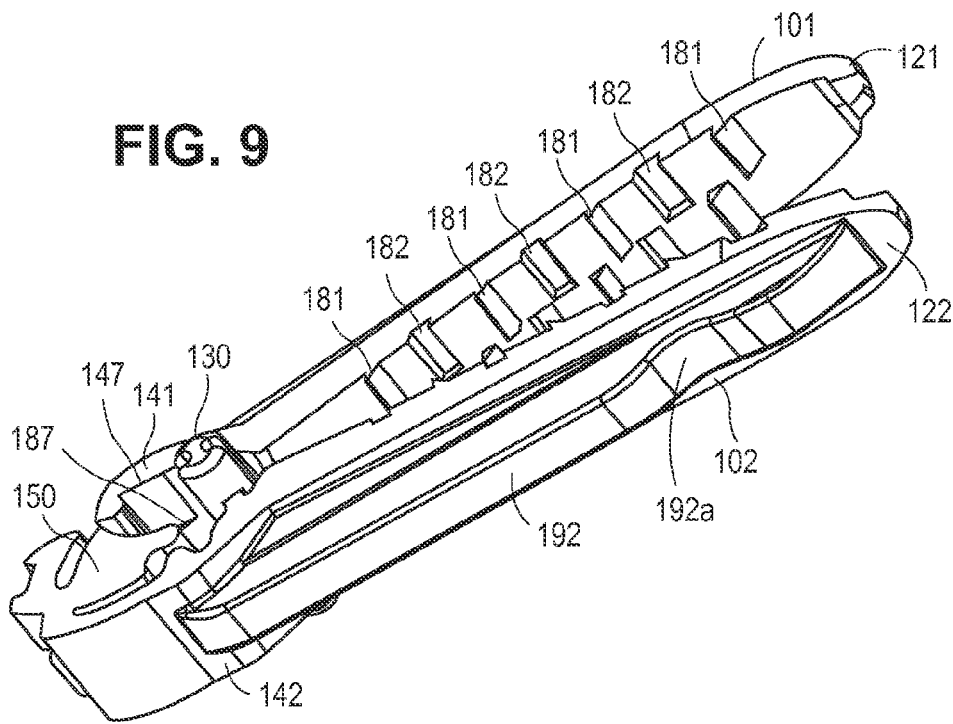
FIG. 9 is a perspective view from the bottom of the clip shown in FIG. 8a in the open position.
Figure 10:
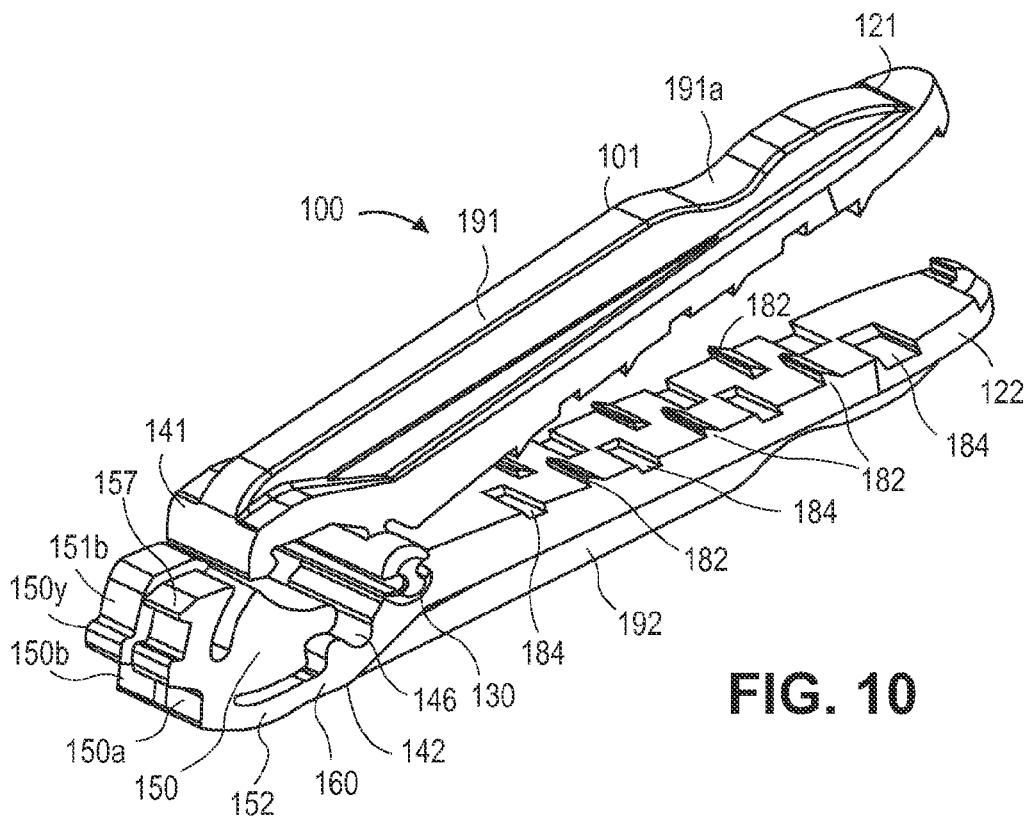
FIG. 10 is a perspective side view from the top of the clip shown in FIG. 8a in the open position.

FIGS. 2a, 2b, and 2c show side, top, and bottom views respectively, of the clip shown in FIG. 1. As shown in FIG. 2b, the wedge or buttress body 150 can be divided into two lateral sections or portions 150a and 150b, each on opposite sides of the longitudinal axis L as shown, and can form approximate lateral halves of the buttress body 150, with a possible space or small channel in-between. Lateral portion 150b of the buttress body 150 can have a width in a plane spanning the transverse and longitudinal axes sufficient to exceed a complementary width formed by the locking space 170 to create an interference fit between the proximal end portion 145 of the curved inner surface 143 of the first jaw structure 141 and the outer surfaces 151a, 151b on the proximal first end portion outer surface 151 of the buttress body 150, to bias the clip in a closed position. An example of the transverse width of said lateral portion 150b is shown as distance "TW1" in FIG. 7a, with complementary width "TW2" being formed by the locking space 170, it being understood that TW1 is slightly greater than TW2 in order to create the interference fit. In the embodiment as shown in FIGS. 1, 2b, and 7a, on lateral portion 150b there is no detent 157, and said lateral portion 150b of the buttress body is formed by a partial lateral width of the buttress body 150. Thus, as shown in FIG. 2b, the notch 147 and detent 157 are formed on corresponding partial lateral sections or slices of the buttress body 150 and first jaw structure 141, respectively, this lateral section 150a of buttress body 150 being on the opposite side thereof to the lateral section 150b. In this manner, the buttress body 150, once locked into place as shown in FIG. 12, is prevented from moving laterally from side to side since the notch 147 and detent 157 interlock only extends laterally partially across the clip, the detent 157 being limited in lateral movement by a shoulder 187 formed by a termination of the notch 147 laterally into the first jaw structure 141, as shown in FIG. 9. As shown in FIG. 8b, the lateral slice of buttress body 150 only extends for a lateral width LW1 which includes detent 157, which the lateral slice LW2 of buttress body 150 on the other side of the clip does not include the detent 157. In this manner, the proximal locking mechanism of the clip 100 is more stable in lateral directions, which is also useful for keeping all parts of the clip together in the event the living hinge 160 may break.

Figure 5:
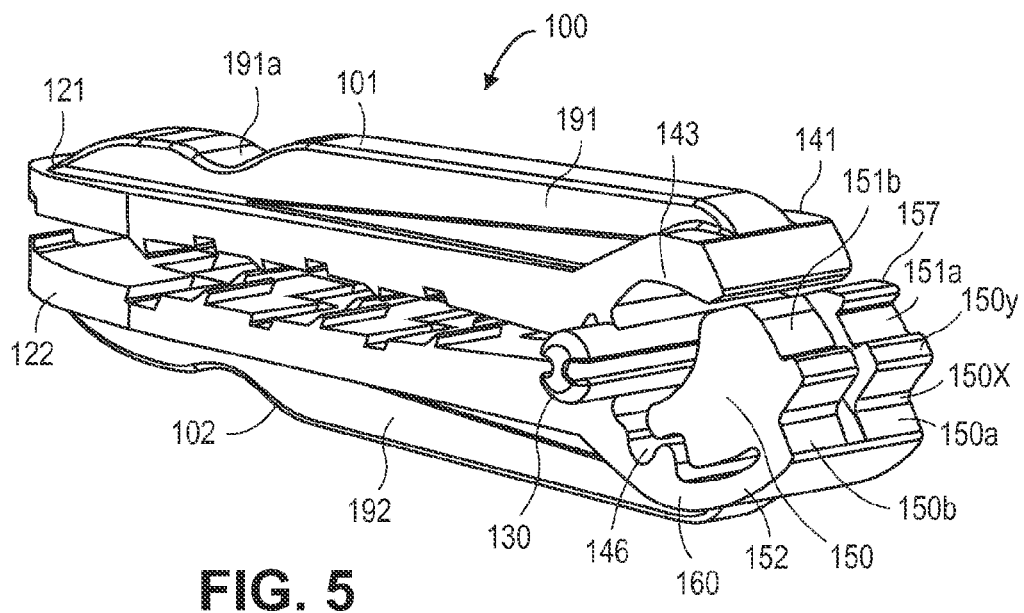
FIG. 5 shows a perspective view of the clip shown in FIG. 1 from the side opposite to that shown in FIGS. 3 and 4.

As best shown on FIG. 5, the outer surface 151 on proximal first end portion of buttress body 150 on a proximal end of the clip 100 defines one or more surfaces which form a curved planar segment abutment portion, which in the embodiment as shown includes curved planar segment abutment portions 151a and 151b. As used herein, the "curved planar segment abutment portion" formed by a surface may include a single curved surface segment or a series of curved or straight planar surface segments connected to one another which form an overall generally curved surface, each of the surface segments extending as a surface at least laterally. In the embodiment shown in FIG. 5, curved planar segment abutment portion 151a included planar and curved surface segments formed by the notch 157 and extends laterally for about one-half of the lateral width of clip 100, curved planar segment abutment portion 151b includes planar and curved surface segments which also extend laterally for about one-half of the lateral width of clip 100. Each of the curved planar segment abutment portions 151a and 151b on outer surface 151 forms a substantial abutment surface that pushes against complementary curved inner surfaces of jaw 141 to provide a stronger and more stable locking mechanism for clip 100. This is provided, at least in part, by the relatively larger and wider surface areas, lateral spans, and segmented surfaces which interlock and abut against each other to provide enhanced holding strength and stability.

Figure 6A:
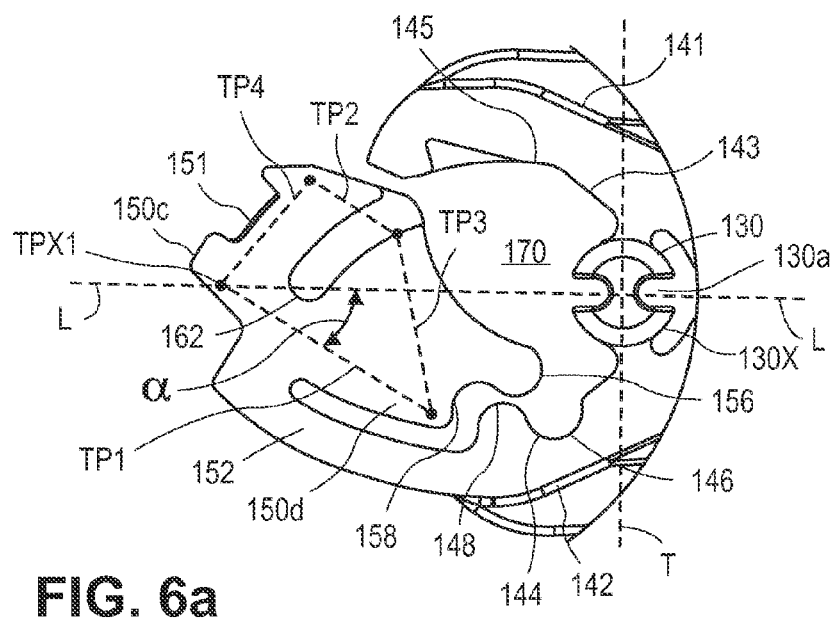
FIG. 6a is a close-up detail view of the portion of the clip shown in FIG. 6 in region "A1" therein.
Figure 6:
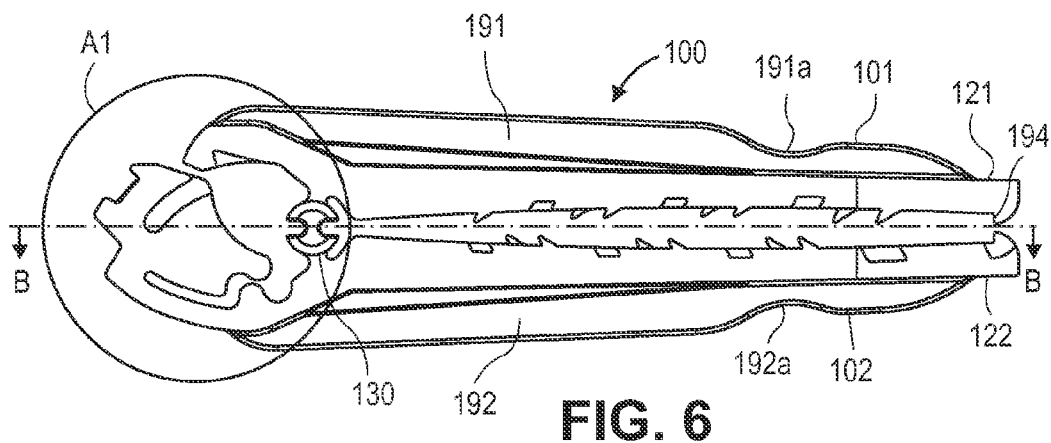
FIG. 6 is another side view of the clip shown in FIG. 1.
Figure 6B:
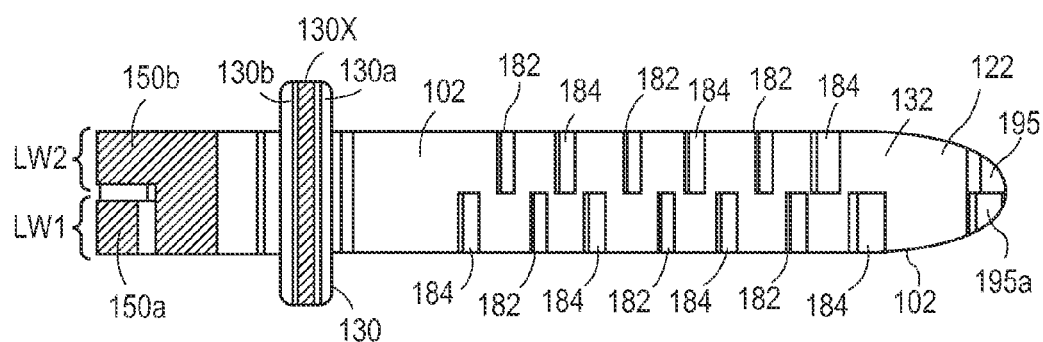
FIG. 6b is a sectional view of the clip shown in FIG. 6 taken along section B-B in the direction shown in FIG. 6.

As best shown in FIG. 6a, the second curved inner surface 144 on the second jaw structure 142 forms a first laterally spanning recessed groove 146 separated from the clip hinge 130 and a first laterally spanning ball-shaped or rounded protruding surface 148 proximal to said recessed groove 146, and a distal second end portion of the buttress body 150 forms a second laterally spanning recessed groove 158 and a second laterally spanning ball-shaped or rounded protruding surface 156 distal to said second recessed groove which are shaped complementary to the first rounded surface 148 and first recessed groove 146, respectively, so as to mate in abutment when the buttress body 150 is pivoted into the locking space 170 to further stabilize and bias the clip in a closed position. The first recessed groove 146, first rounded surface 148, second recessed groove 158, and second rounded surface 156 may extend laterally all the way across the lateral width of the buttress body 150, such that the first rounded surface 148 and second rounded surface 156 are not spherically shaped but rather form an extended, laterally-spanning, rounded, semi-cylindrical surface which can mate in corresponding semi-cylindrical shaped grooves formed by first recessed groove 146 and second recessed groove 158.

As shown in FIG. 6a, the buttress body 150 can further define a second living hinge 162 extending laterally between the proximal first end portion 150c of buttress body 150 and a distal second end portion 150d, wherein the proximal first end portion 150c including outer surface 151 further pivots about said second living hinge 162 when the buttress body 150 moves into the locking space 170, allowing the outer surface 151 of the proximal first end portion 150c of the buttress body to flex towards the longitudinal axis L prior to abutment against the curved inner surface 143 of the first jaw structure 141.

As best shown in FIGS. 5 and 12, the outer surface of the proximal end of the buttress body 150, or clip 100 itself, defines a V- or L-shaped laterally spanning notch 150x on the proximal end of the clip 100 and further defines a laterally spanning flange 150 y extending from said notch 150x adjacent to the curved planar segment abutment portions 151a and 151b. Each of notch 150x and flange 150y may be divided into two lateral sections or components divided by a small space or channel therebetween as they are disposed on the lateral sectional halves 150a and 150b of the buttress body 150. The notch 150x provides a receiving space for the tip of an instrument, pushing or actuating rod, or another clip, so as to enable a more stable actuation of the buttress body 150 into locking space 170 to lock the clip 100. The flange 150y may act to limit the movement of buttress body 150 once fully inserted into locked position inside space 170, and also further stabilizes the locking mechanism for the clip 100.

Figure 13:
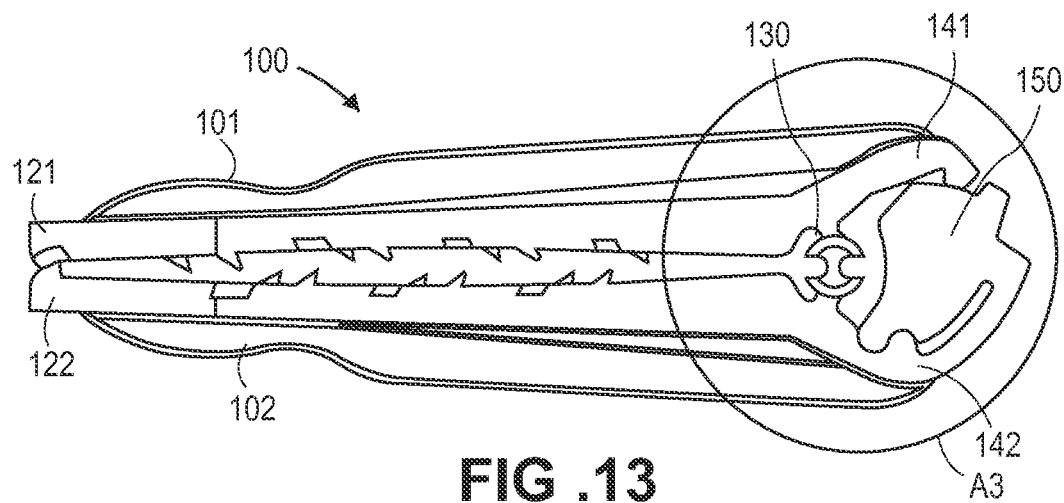
Figure 13A:
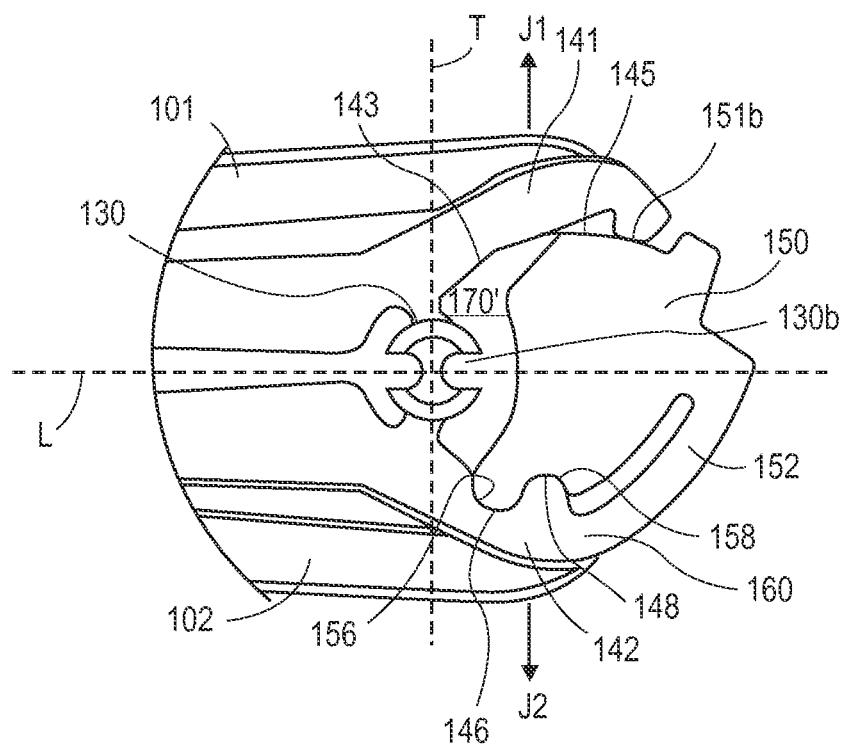
FIG. 13a is a close-up detail view of the portion of the clip shown in FIG. 13 in region "A3" therein.

In the embodiment shown in FIGS. 1-15, the buttress body may occupy a majority of a volume defined by locking space 170 when it is moved into clip locked position so as to bias the legs 101, 102 in a closed position. The volume defined by the locking space is limited by the lateral width of the clip legs 101, 102 near the hinge 130 and the jaws 141 and 142. As shown in FIG. 13a, the remaining locking space 170' between jaws 141 and 142, once the clip is locked by movement of the buttress body 150 into space 170, is less than half the volume of the locking space 170 as shown in FIG. 6a. The presence of a bulky body like buttress body 150 which occupies the majority of the volume or space between proximal extending jaws 141 and 142 when the clip 100 is in the locked position further provides a greater strength and stability to the locking of said clip.

In the embodiment shown in FIGS. 1-15, and as shown in detail in FIG. 6a, the buttress body 150 can be characterized in one way as having a core mass which has, in a transverse plane spanning the longitudinal and transverse axes, a cross-section which approximately spans a trapezoidal shape, having rounded curved sides extending from the sides TP1, TP2, TP3, TP4 of the trapezoid. Side TP1 defines the longest side and one of the parallel sides of the trapezoid, while side TP2 defines the shorter parallel side. Side TP3 defines the longer and more distal of the non-parallel sides, while side TP4 defines the shorter and more proximal non-parallel side. Side TP1 is therefore connected to sides TP3 and TP4. When the clip is in the unlocked position as shown in FIG. 6a, and the buttress body 150 is fully extended away from the clip hinge 130 out in the most proximal position, the vertex TPX1 of sides TP1 and TP4 lies approximately on or near the longitudinal axis L, and side TP1 makes an angle α below the longitudinal axis, towards proximal jaw 142, such angle α being, in one embodiment, approximately 30 degrees. As shown in FIG. 6a, the rounded laterally-spanning protuberance 156 extends substantially from side TP3.

The clip hinge 130 can be a resilient hinge providing additional biasing force to maintain the inner clamping surfaces 131, 132 of the legs towards a closed position. A span of each leg extending from the clip hinge 130 to its respective distal tip 123, 124, can be, in one embodiment of the present invention, at least 75% to 80% of an overall length of the clip. As shown in FIGS. 2b and 2c, the clip hinge 130 can define lateral bosses which extend laterally from the side surfaces of the clip legs, defining a bossed width or span which is greater than the clip width.

In the embodiment shown in FIGS. 1-15, the clip hinge 130 is formed as a laterally extending trunnion or bar 130x integrally formed with the first and second legs 101, 102, each leg being resiliently coupled to first and second transverse sides of said bar, the bar 130x further defining laterally spanning grooves 130a and 130b on longitudinally distal and proximal sides of the bar, respectively. These grooves 130a and 130b further enable the clip 100 to flex as pivoting about the lateral axis of hinge 130, and further provide a resilient pivoting moment or force about said hinge.

Furthermore, in the embodiment shown in FIGS. 1-15, flanges 191 and 192 extend longitudinally across respective outer surfaces of each of the first and second legs 101, 102 which are on opposite sides to the inner clamping surfaces 131, 132 of each respective leg, the flange 191 of the first leg 101 extending from the first jaw structure 141 to the distal end portion 121 of the first leg 101, the flange 192 of the second leg 102 extending from the second jaw structure 142 to the distal end portion 122 of the second leg 102. Each of the flanges 191, 192 defines a transverse indentation 191a, 192a proximate the distal end portions 121, 122 of the legs 101, 102. The flanges 191 and 192 provide a rigidity to legs 101 and 102, respectively, such that said legs do not easily bend. Transverse indentations 191a and 192a provide a means for a clip applier to better actuate or grip the legs 101, 102.

The clip 100 further includes serrations, ridges, or teeth 181, 182 on the inner clamping surfaces 131 and 132, respectively, as shown in FIGS. 6b and 7b, and 9, 10, and 15a. The teeth or ridges 181, 182 provide additional grasping means to better attach and clamp the clip 100 onto a vessel when closed. The teeth or ridges 181, 182 are disposed to fit into complementarily arranged grooves 183 and 184 on the clamping surfaces 131 and 132, respectively. The teeth 181, 182 may have a slanted orientation, extending proximally, so as to better grip tissue. As best shown in FIGS. 6-6a and 7-7a, a pair of distal hook elements 194 and 195 may be disposed on the absolute distal tips of legs 101 and 102, respectively, each hook 194 and 195 offset laterally with respect to each other to form a scissor-like configuration, such that each hook 194 and 195 fit into corresponding recesses 195a and 194a, respectively, on the distal tips of legs 102 and 101, respectively. This mechanism provides means to further grip and contain tissue with the space between the clamping surfaces 131, 132 when the clip 100 is applied to body vessel.

Figure 15:
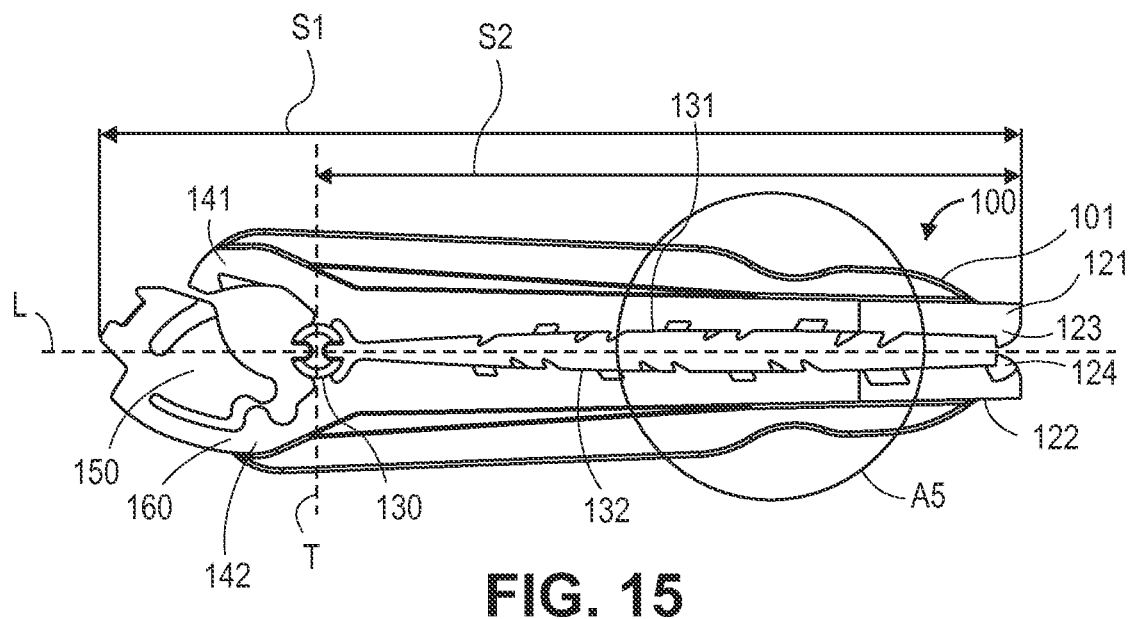
FIG. 15 is a view of the clip shown in FIG. 1.
Figure 15A:
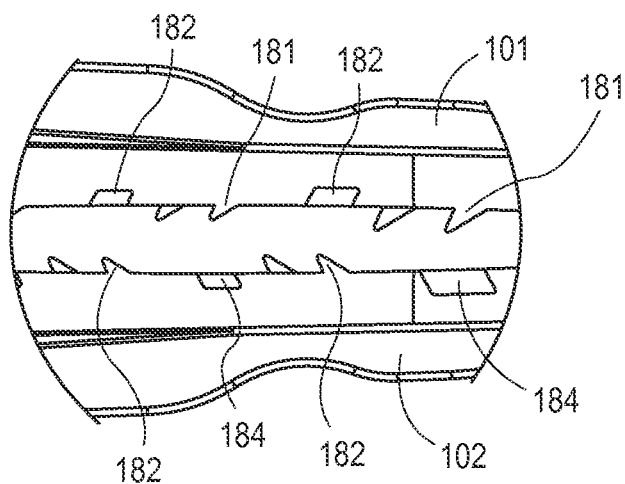
FIG. 15a is a close-up detail view of the portion of the clip shown in FIG. 15 in region "A5" therein.

The clip 100 may be in a range of sizes. As shown in FIG. 15, an overall length "S1" of the clip 100 may be approximately 0.50 inches; the length "S2", between the intersection of transverse axis T and longitudinal axis L centered at clip hinge 130 and the distal tip of the clip, may be approximately 0.40 inches, and the radius of curvature of the inner mating or clamping surfaces 131, 132 of the legs 101, 102 may be approximately 3.0 inches. Such sizes and dimensions are given as an example, and it is understood that the clip 100 may, in one or more embodiments, vary in size ranging from approximately 0.15 to 0.80 inches in overall longitudinal length, and from approximately 0.03 to 0.15 inches in lateral width. As one particular embodiment, the illustration of clip 100 in FIG. 15 is shown as a scaled magnification of actual size, and shows all the parts of the clip 100 in actual proportion to each other.

FIGS. 19a-f show another embodiment of the invention, of clip 1400. Clip 1400 is similar to clip 100 in many respects, as described herein, wherein similar features as shown in FIGS. 19a-f are as described in clip 100 in FIGS. 1-15a. Clip 1400 however includes features missing in clip 100, which provide a new and useful inventive surgical ligation clip. In clip 1400, a clip hinge 1430 joins the first and second legs 1401, 1402 at a point on their respective proximal end portions 1411, 1412, the first and second legs each having respective inner clamping surfaces 131, 132 between the clip hinge 1430 and the distal ends 121, 122 of said first and second legs, the clamping surfaces being apposed when the clip is in a fully closed position, similar to the apposition of inner clamping surfaces in clip 100 discussed above. The clip hinge 1430 in the particular embodiment shown in FIGS. 19a-f includes a laterally-spanning, trunnion-like bar element which extends laterally past the width of clip legs 1401, 1402, similar to clip hinge means 130. In clip 1400, a first jaw structure 1441 on the first leg 1401 extends proximal to a transverse axis "T" which is perpendicular to both the longitudinal axis L and lateral pivot axis P, all intersecting at a point centered on the clip hinge 1430. The first jaw structure 1441 includes a first curved inner surface 1443. In clip 1400, a second jaw structure 1442 is on the second leg 1402 extending proximal to the transverse axis T and has a second curved inner surface 1444 extending from the clip hinge 1430. In clip 1400, both of jaws 1441 and 1442 are each substantially proximal to a transverse plane extending through transverse axis T and lateral pivot axis P, thus behind or proximal to the clip hinge 1430, thereby providing a means for actuating the clip legs 1401 and 1402 and biasing or locking the clip 1400 and its mating faces 131, 132 in a closed position, which biasing or locking means can be actuated and/or applied by acting substantially only on the proximal end portions of the clip 1400, without having to lock the distal ends 121, 122 to each other or use a clip applier tool which acts on said distal ends.

Figure 19A:
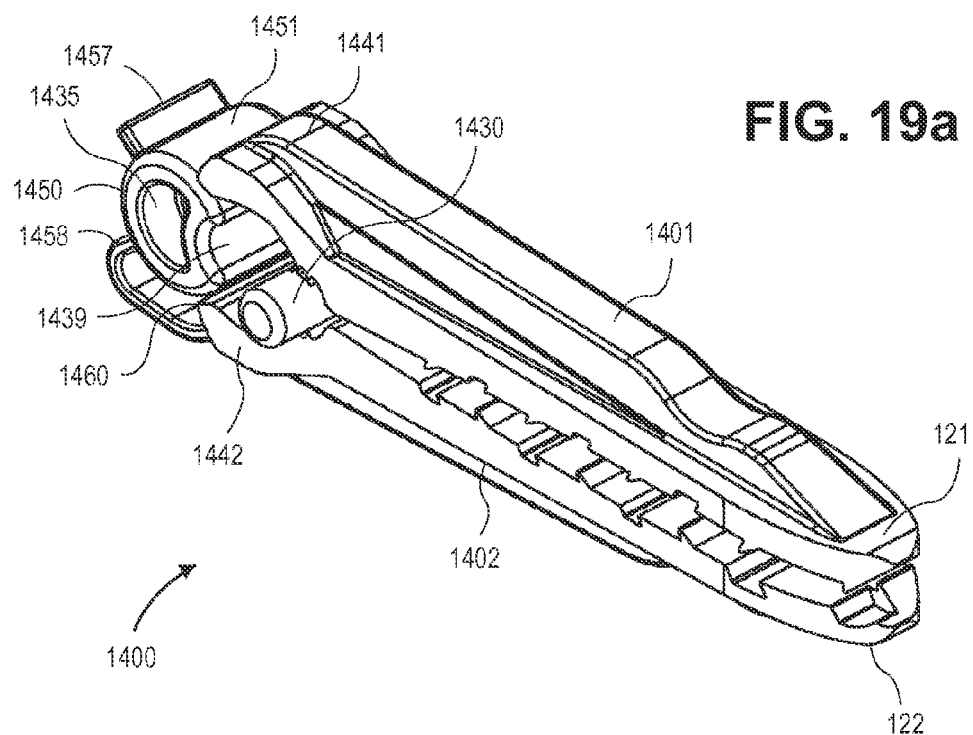
FIG. 19a is a view of a surgical ligation clip according to another embodiment of the invention.
Figure 19B:
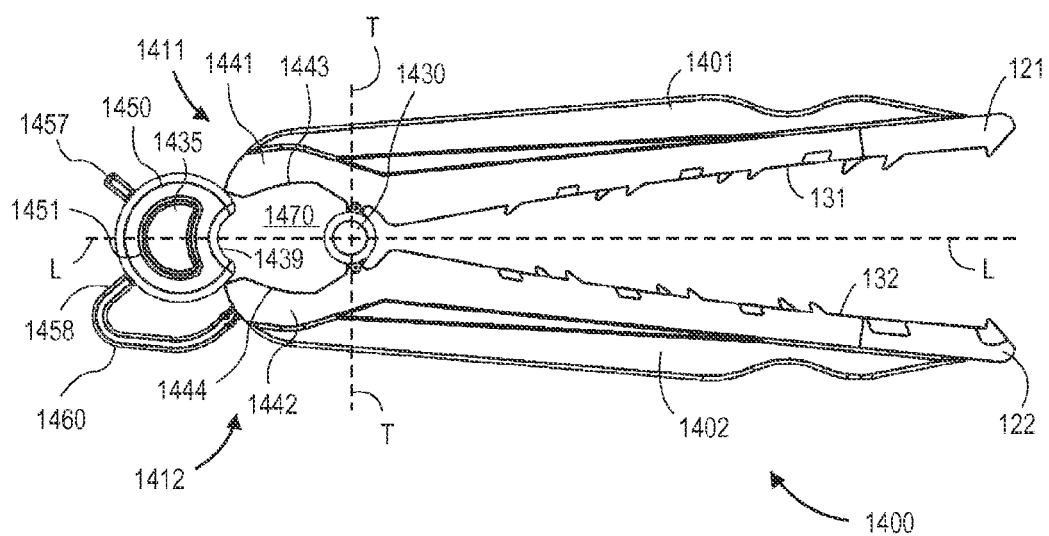
FIG. 19b is a side view of the surgical ligation clip of FIG. 19a, with the clip legs substantially open.

Clip 1400 differs at least on one respect from clip 100 in that the curved inner surfaces 1443 and 1444 of proximally-extending jaws 1441 and 1442, respectively, are substantial mirror-images of each other across the longitudinal axis when viewed in the plane of FIG. 19b, such that the surfaces 1443 and 1444 define a locking, receiving, or socket space 1470 therebetween, each of surfaces 1443 and 1444 being substantially concave facing each other from opposite sides of the longitudinal axis L. The socket space 1470 is sized and shaped to accept a buttress body 1450 forming a substantially cylindrical body 1451 spanning laterally on a proximal end of the clip 1400. The buttress body 1450 can be pivoted about a connecting hinge or web 1460 which couples the substantially cylindrical body 1451 with the second proximal jaw structure 1442 as shown in FIG. 19b. Once the cylindrical body 1451 is pivoted into socket space 1470, which also defines a substantially cylindrical receiving space for the cylindrical body 1451, the jaws 1441 and 1442 are biased outwards from longitudinal axis L to bias the legs 1401 and 1402 of clip 1400 closed, as shown in FIGS. 19e and 19f.

In clip 1400, buttress body 1450 further includes at least one flange 1457 spanning laterally across an outer proximal surface portion of cylindrical body 1451 of the buttress body 1450, which helps to stabilize and keep the buttress body 1450 centered in socket space 1470 once in the locked position shown in FIGS. 19e and 19f. A portion of connecting web 1460 terminates in an angled connection 1458 which is shaped and oriented similar to flange 1457 for the same purpose. In clip 1400, the buttress body 1450 defines at least one recess 1435 extending laterally inwards into a lateral side of the cylindrical body 1451 of said buttress body 1450, which aids in movement or actuation of the buttress body 1450 and hence locking mechanism of clip 1400. A recess 1435 may exist on both lateral sides of cylindrical body 1451, as shown in FIGS. 19e and 19f.

In clip 1400, the buttress body 1450 further defines a groove 1439 extending laterally across an outer distal surface portion 1453 of the cylindrical body 1451 of said buttress body 1450. The groove 1439 is shaped to mate or abut against a complementary cylindrical surface 1438 of the proximal side of bar or trunnion-shaped clip hinge means 1430.

FIGS. 20*a* and 20*b* show a variant of clip 1400, as clip 1400*x*, which includes legs 1401 and 1402 having proximal jaw portions 1441 and 1442, respectively, and being hinged together at clip hinge means 1430*x*, which is substantially similar to clip hinge means 1230 in clip 1200. In clip 1400*x*, buttress body 1450*x* differs from buttress body 1450 in clip 1400 in that flange 1457*x* extends as a laterally-spanning curved web or flange extending from a proximal side surface of cylindrical body 1451 in buttress body 1450*x*, which assists in guiding and positioning buttress body 1450*x* when actuated. In one embodiment, an inner concave surface of flange 1457*x* may fit over the proximal end surface of proximal jaw 1441, further stabilizing the buttress body 1450*x* when actuated into the socket space 1470.

FIGS. 16*a*-16*c*, 17*a*-17*c*, and 18*a*-18*c* show another embodiment of the invention, of clip 1500. Clip 1500 is similar to clip 1400 and 1400*x* in many respects, having similar features as may be commonly shown in the figures, and including but not limited to the potential size of the clip or clip legs, or materials used. In clip 1500, a clip hinge 1530 joins the first and second legs 1501, 1502 at a point on their respective proximal end portions 1511, 1512, the first and second legs each having respective inner clamping surfaces 1531, 1532 between the clip hinge 1530 and the distal ends 1521, 1522 of said first and second legs, the clamping surfaces being substantially apposed when the clip is in a fully closed position, similar to the apposition of inner clamping surfaces in clips 100, 1400, and 1400*x* discussed above. In clip 1500, a first jaw structure 1541 on the first leg 1501 extends proximal to a transverse axis "T" which is perpendicular to both the longitudinal axis L and lateral pivot axis P, all intersecting at a point centered on the clip hinge 1530. The first jaw structure 1541 includes a first curved inner surface 1543 extending from the clip hinge 1530. In clip 1500, a second jaw structure 1542 is on the second leg 1502 extending proximal to the transverse axis T and has a second curved inner surface 1544 extending from the clip hinge 1530. In clip 1500, both of jaws 1541 and 1542 are each substantially proximal to a transverse plane extending through transverse axis T and lateral pivot axis P, thus behind or proximal to the clip hinge 1530, thereby providing a means for actuating the clip legs 1501 and 1502 and biasing or locking the clip 1500 and its mating faces 1531, 1532 in a closed position, which biasing or locking means can be actuated and/or applied by acting substantially only on the proximal end portions of the clip 1500, without having to lock the distal ends 1521, 1522 to each other or use a clip applier tool which acts on said distal ends.

Figure 16A:
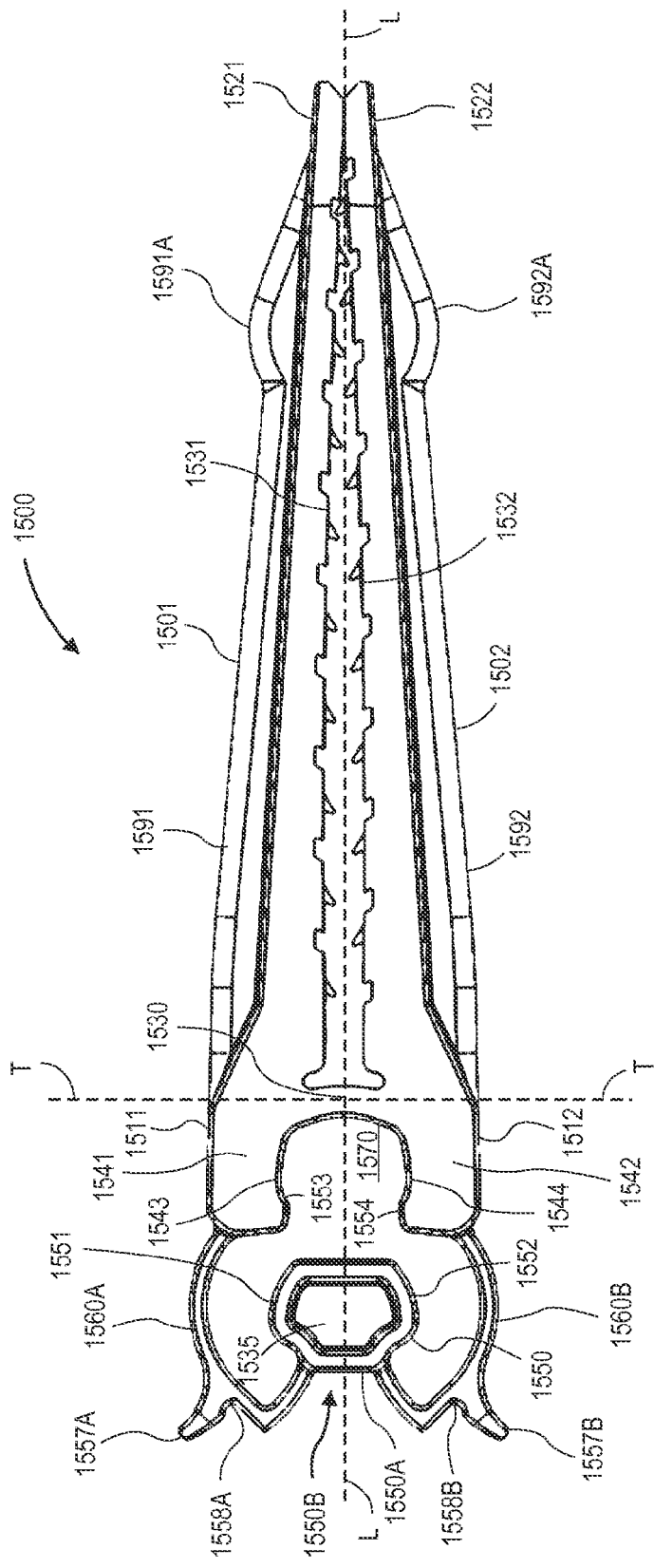
FIGS. 16a and 16b-16c are side and perspective side views of a surgical ligation clip according to another embodiment of the invention.
Figure 18A:
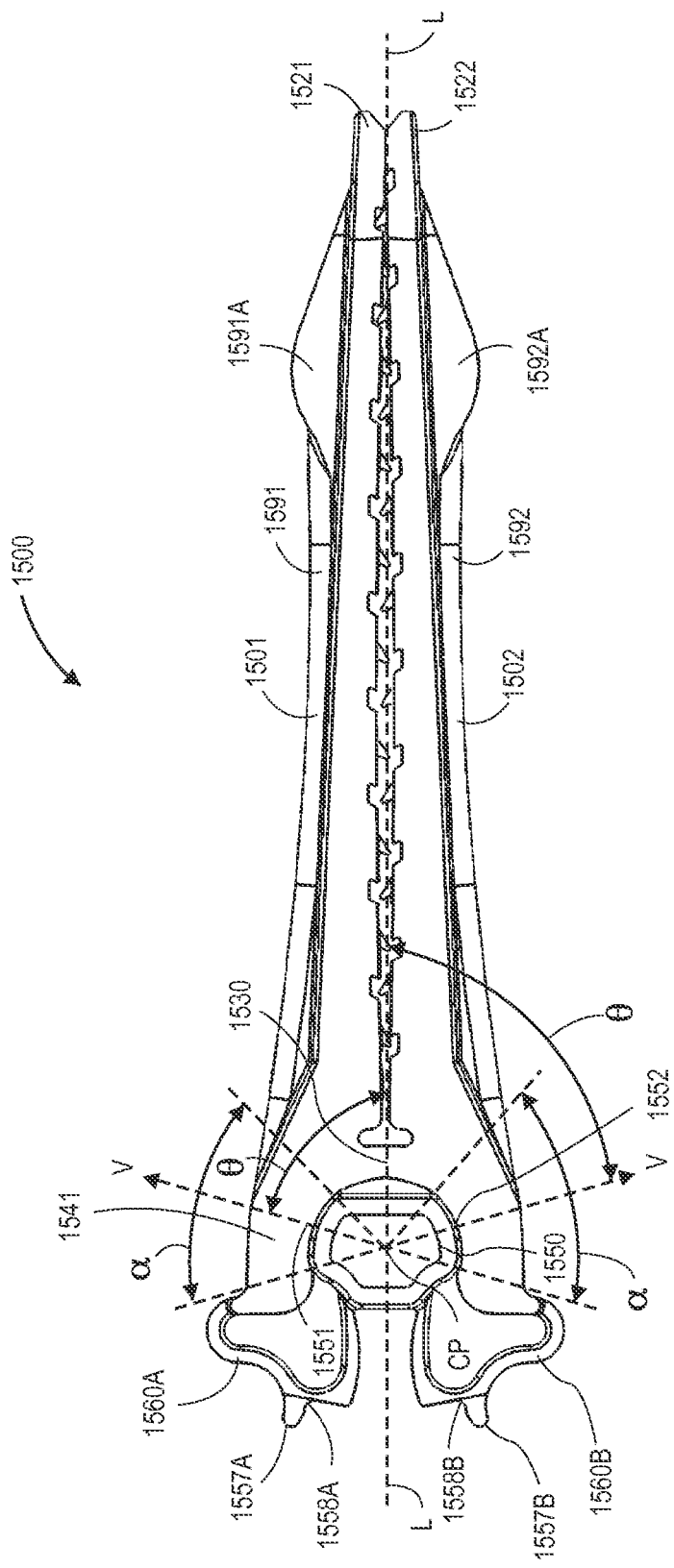
FIGS. 18a and 18b-18c are side and perspective side views of the clip shown in FIGS. 16a-16c, with the clip legs fully closed and the clip in a locked position.
Figure 18B:
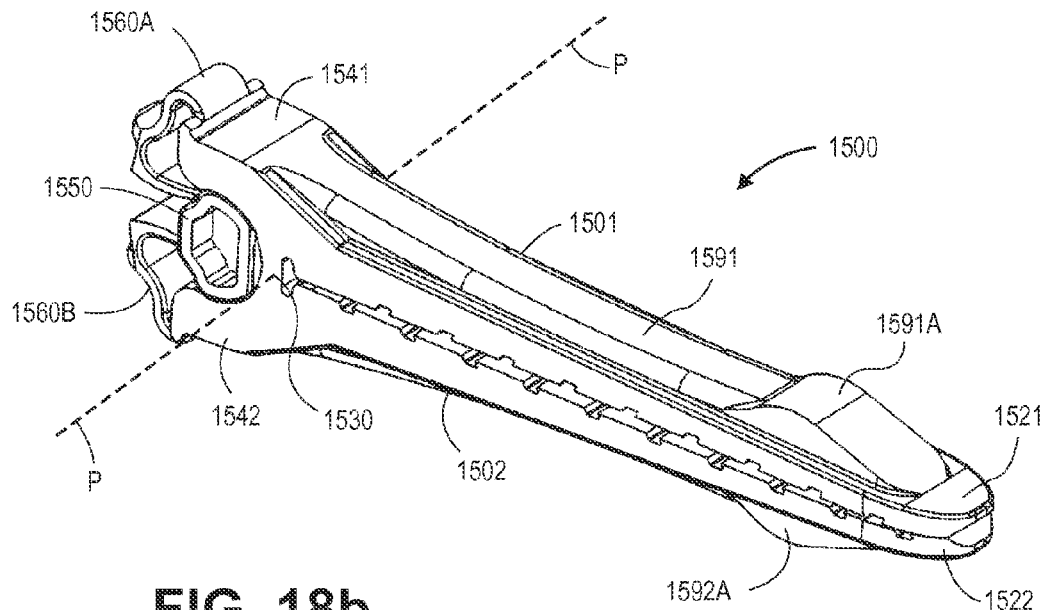
Figure 18C:
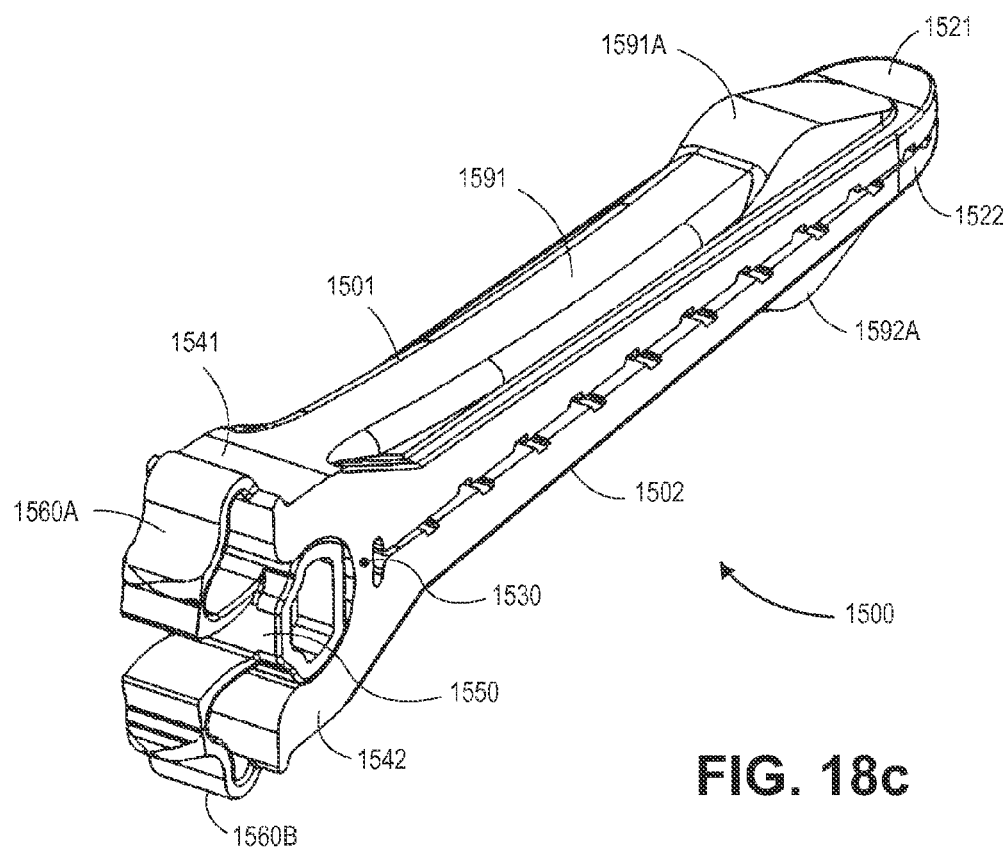

In clip 1500, the curved inner surfaces 1543 and 1544 of proximally-extending jaws 1541 and 1542, respectively, are substantial mirror-images of each other across the longitudinal axis when viewed in the plane of FIG. 16*a*, such that the surfaces 1543 and 1544 define a locking, receiving, or socket space 1570 therebetween, each of surfaces 1543 and 1544 being substantially concave facing each other from opposite sides of the longitudinal axis L. The socket space 1570 is sized and shaped to accept a buttress body 1550, which can define an outer perimeter of a generalized cylinder, whose transverse cross-section can be any curve, but as shown in the embodiment of FIG. 16*a* is preferably in the shape of a substantially cylindrical body spanning laterally on a proximal end of the clip 1500, preferably across the full lateral width of the clip 1500 such as across the proximal jaws 1541, 1542. The buttress body 1550 can be moved, generally along a direction parallel to longitudinal axis L by an actuation force applied to the proximal side of body 1550, into the locking or socket space 1570 while said buttress body 1550 is connected via connecting hinges or webs 1560A, 1560B, which are a type of living hinge, which each couple the buttress body 1550 with the ends of the proximal jaw structures 1541 and 1542 as best shown in FIG. 16*a*. Once the buttress body 1550 is moved into socket space 1570, which also defines a substantially cylindrical receiving space for the substantially cylindrical buttress body 1550, the jaws 1541 and 1542 are pushed outwards from longitudinal axis L to bias the legs 1501 and 1502 of clip 1500 closed, as shown in FIGS. 18*a*-18*c*. At least first and second curved planar segment abutment portions 1551 and 1552 of the outer surface of the buttress body 1550 each abuts against the substantially concave curved inner surfaces 1543 and 1544, respectively, of the first and second jaw structures 1541 and 1542, respectively, to bias the clip 1500 in a closed position. The mating of these surfaces, and/or the mass, volume subtended, or full lateral span of the buttress body 1550, provides for a stronger and more stable locking mechanism, as more further described herein.

In the embodiment shown in FIG. 16*a*, the first and second curved planar segment abutment portions 1551 and 1552 of the outer surface of the buttress body 1550 each form a convex outer surface when generally facing the longitudinal axis and which are complementary to the substantially concave curved inner surfaces 1543 and 1544 of the first and second jaw structures 1541 and 1542, respectively. In the embodiment shown in FIG. 16*a*, the convex first and second curved planar segment abutment portions 1551 and 1552 of the outer surface of the buttress body 1550 are preferably symmetrical about the longitudinal axis and the substantially concave curved inner surfaces 1543 and 1544 of the first and second jaw structures 1541 and 1542 are preferably symmetric about the longitudinal axis. Furthermore, in the embodiment shown in FIG. 16*a*, the proximal end of each of the curved inner surfaces 1543 and 1544 of the first and second jaw structures 1541 and 1542, respectively, forms a lip 1553 and 1554 at a proximal end of each jaw structure 1541 and 1542, respectively, extending transversely inwardly towards the longitudinal axis L to grip against the proximal ends of each of the first and second curved planar segment abutment portions 1551 and 1552, respectively, of the outer surface of the buttress body 1550 when said body is moved in the locking space, as shown in FIG. 18*a*.

As best shown in FIG. 18*a*, an embodiment of the clip 1500 may be configured such that a vector V from a centerpoint lateral axis CP of the buttress body 1550 through a midpoint lateral span of either of the convex first and second curved planar segment abutment portions 1551 and 1552 of the outer surface of the buttress body 1550 forms an angle Θ of about 65 to 80 degrees, or more preferably 70 to 75 degrees, from the longitudinal axis L. In such embodiment, the convex first and second curved planar segment abutment portions 1551 and 1552 each form a surface spanning a sector of about 60 to 70 degrees about such centerpoint lateral axis CP. This configuration of surface segments 1551 and 1552 which abuts against complementary substantially concave curved inner receiving surfaces 1543 and 1544 of the first and second jaw structures 1541 and 1542, respectively, creates a stronger and more stable locking mechanism for the clip 1500 when the buttress body is moved into the locking space 1570, as shown in FIG. 18*a*, by providing a series of forces acting on proximal structures 1541 and 1542 which create moments acting about hinge 1530 that effectively urge the clip legs 1501 and 1502 to remain closed and further supply a superior clamping force between them.

In the embodiment shown in FIG. 16a, the buttress body 1550 forms a substantially cylindrical or generalized cylindrical body spanning laterally on a proximal end of the clip, wherein the locking space 1570 is a socket space and a volume subtended by the buttress body can occupy substantially all of said socket space. The presence of the mass of the buttress body 1550 which displaces nearly all of the volume subtended between the curved inner receiving surfaces 1543 and 1544 of the first and second jaw structures 1541 and 1542, respectively when such buttress body 1550 is moved in the locking space 1570 further provides stability to the locking of clip 1500, such that the clip is less likely to deviate from such locked position due to the relatively low deformability or potential of dislodgement of the buttress body 1550 in such locking space 1570. In the embodiment shown in FIG. 16a, a transverse cross-section of the buttress body 1550 is substantially hexagonal having at least a plurality of curved side segments. Furthermore, the buttress body 1550 can define at least one recess 1535 extending laterally inwards into a lateral side of the body 1550, which can aid in movement or actuation of the buttress body 1550 and hence locking mechanism of clip 1500. A recess 1535 may exist on both lateral sides of body 1550.

Figure 17A:
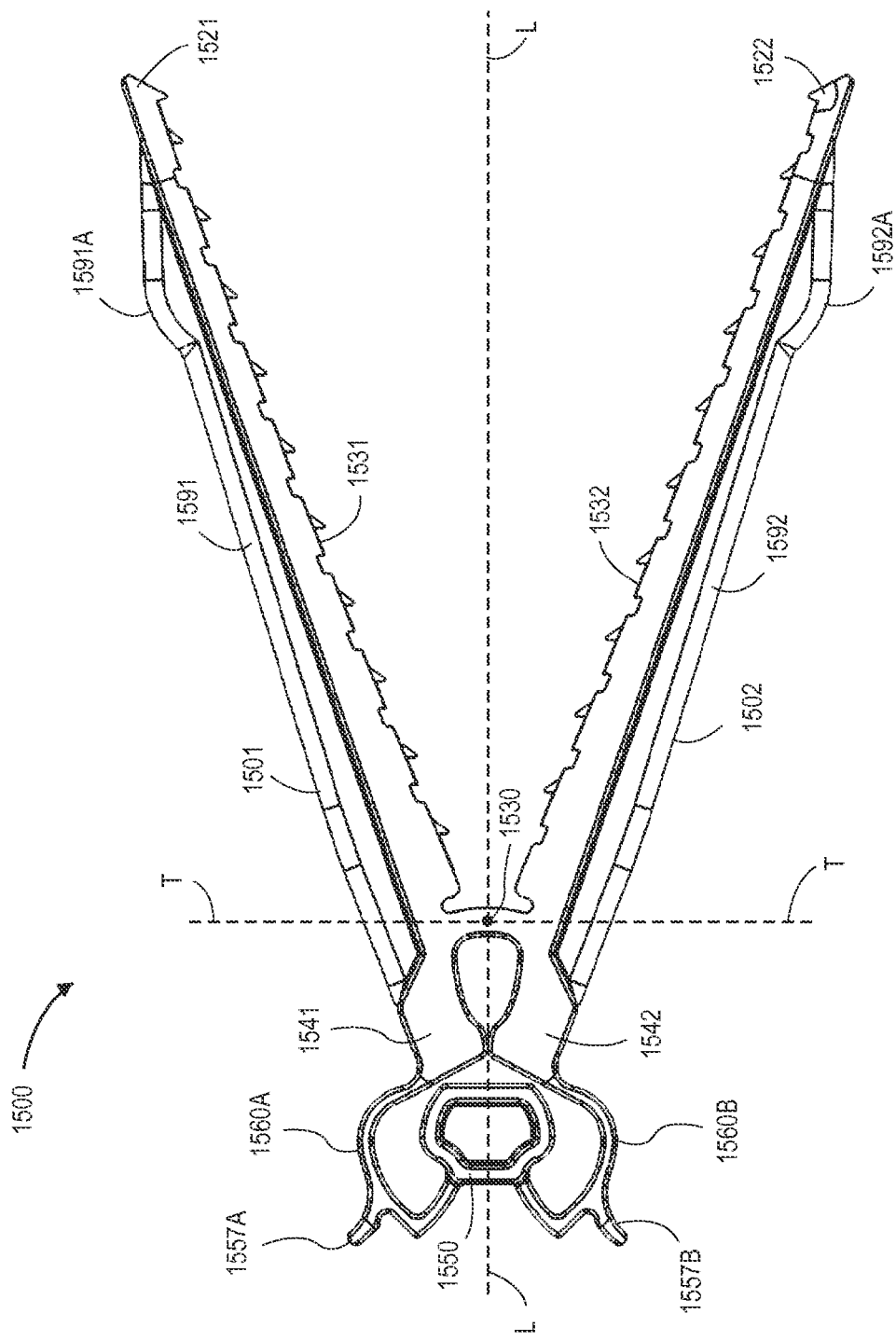
FIGS. 17a and 17b-17c are side and perspective side views of the clip shown in FIGS. 16a-16c, with the clip legs substantially open.

In clip 1500, connecting hinges or webs 1560A, 1560B each connect to a proximal end portion of the buttress body 1550, such that, in an unlocked condition, the buttress body 1550 is positioned entirely proximal to and spaced from the first and second jaw structures 1541, 1542. In this way, the buttress body 1550 tends to be centered on the longitudinal axis outside the locking space 1570 and during movement into said locking space. Furthermore, connecting hinges or webs 1560A, 1560B each can include at least one flange 1557A, 1557B, respectively, extending proximally at an angle from the longitudinal axis L and spanning laterally across an outer proximal surface portion of said connecting hinges or webs 1560A, 1560B, whereby a corresponding notch 1558A, 1558B is formed transversely just inside of each flange 1557A, 1557B. The connecting hinges or webs 1560A, 1560B and/or notches 1558A, 1558B can be used to stabilize and center the orientation of the clip 1500 as multiple clips 1500 are fed through an applier, such as when the open distal ends of a second clip are positioned in notches 1558A, 1558B. Alternatively, the closed distal ends of a second clip can be fed along the longitudinal axis to press against the proximal end face 1550A of the buttress body 1550 to move the first clip and/or actuate and move to buttress body 1550 from a position external to the locking space 1570 as shown in FIG. 16a to a position inside the locking space 1570 as shown in FIG. 18a. This may be facilitated by the presence of a central proximal end notch or recess 1550B which is formed between proximal end portions of the connecting hinges or webs 1560A, 1560B which bow proximally outwards from the buttress body 1550. As further shown in FIG. 17a, the bowing of webs 1560A, 1560B proximally and transversely outwards away from buttress body 1550 as each extends to the proximal end of jaw structures 1541, 1542, respectively, provides a more stable and robust coupling of the buttress body 1550 proximal to and initially spaced from the rest of the clip 1500, which allows clip legs to open more widely as shown in FIG. 17a, such that only the abutment of jaw structures 1541, 1542 against each other limit of such opening. The buttress body 1550 initially does not prevent or impede such opening.

Figure 17B:
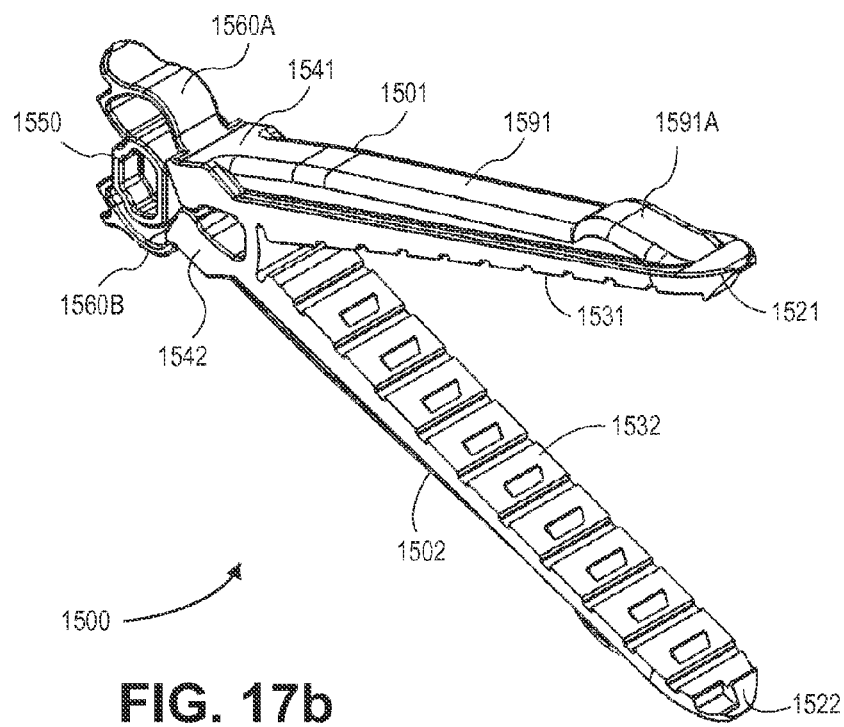
Figure 17C:
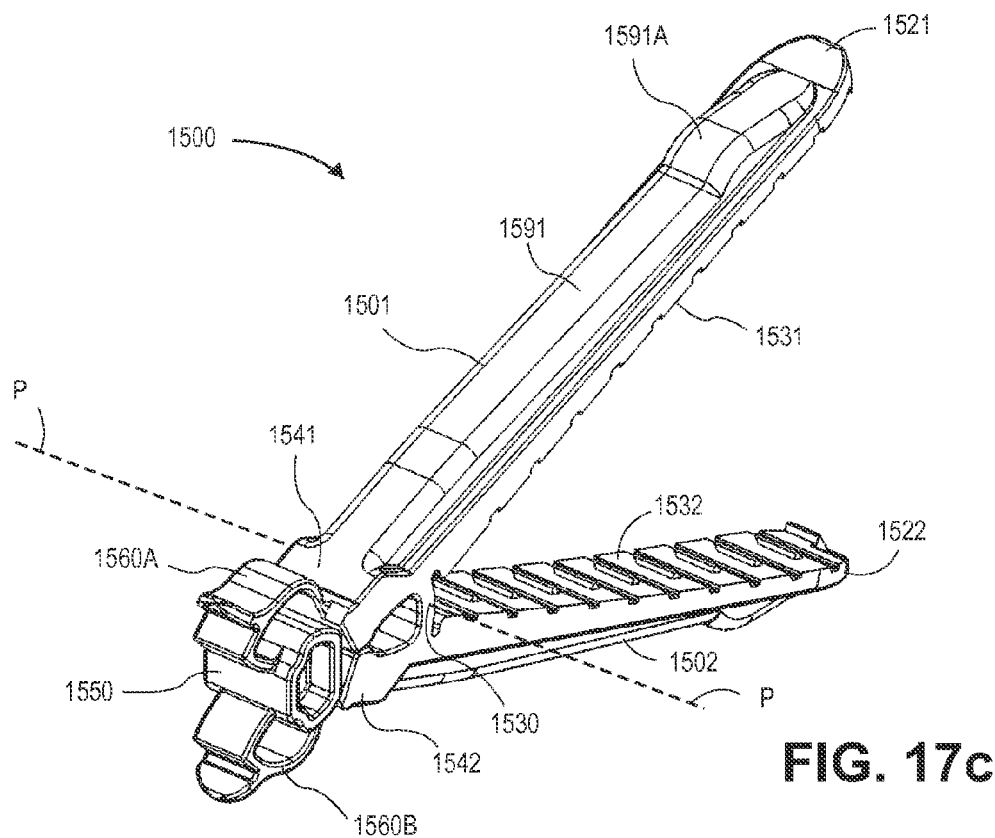

In the embodiment shown in FIG. 16a, and as best shown in FIGS. 17b and 17c, each of the inner clamping surfaces 1531, 1532 define a plurality of teeth and grooves, the teeth and grooves on the first leg 1501 being aligned complementary to grooves and teeth 1502, respectively, of the second leg, as arranged and shown in FIGS. 17b and 17c. Prior to locking the clip 1500 about a vessel, in an initial position as shown in FIG. 16a, each of the inner clamping surfaces 1531, 1532 defines a concave radius of curvature when facing transversely away from the longitudinal axis towards said inner clamping surface. However, when the clip 1500 is closed and locked as shown in FIG. 18a, the curvature of legs 1501, 1502, and hence the inner clamping surfaces 1531, 1532, is more straightened due to the apposition forces provided by the moments about clip hinge 1530 from the jaw structures 1541 and 1542 being urged apart by buttress body 1550.

Figure 16B:
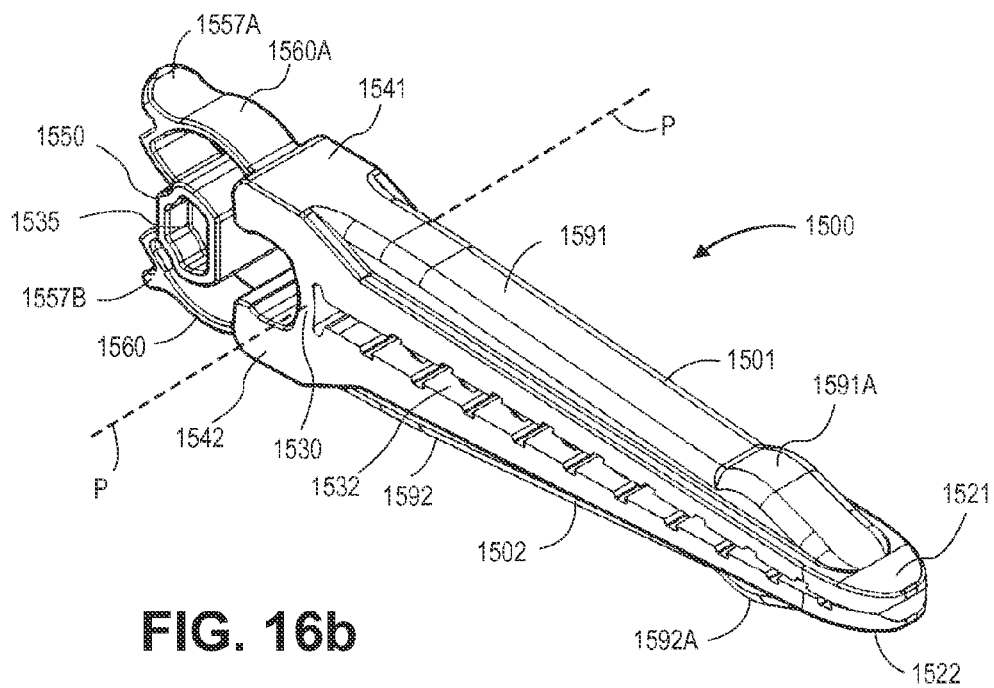
Figure 16C:
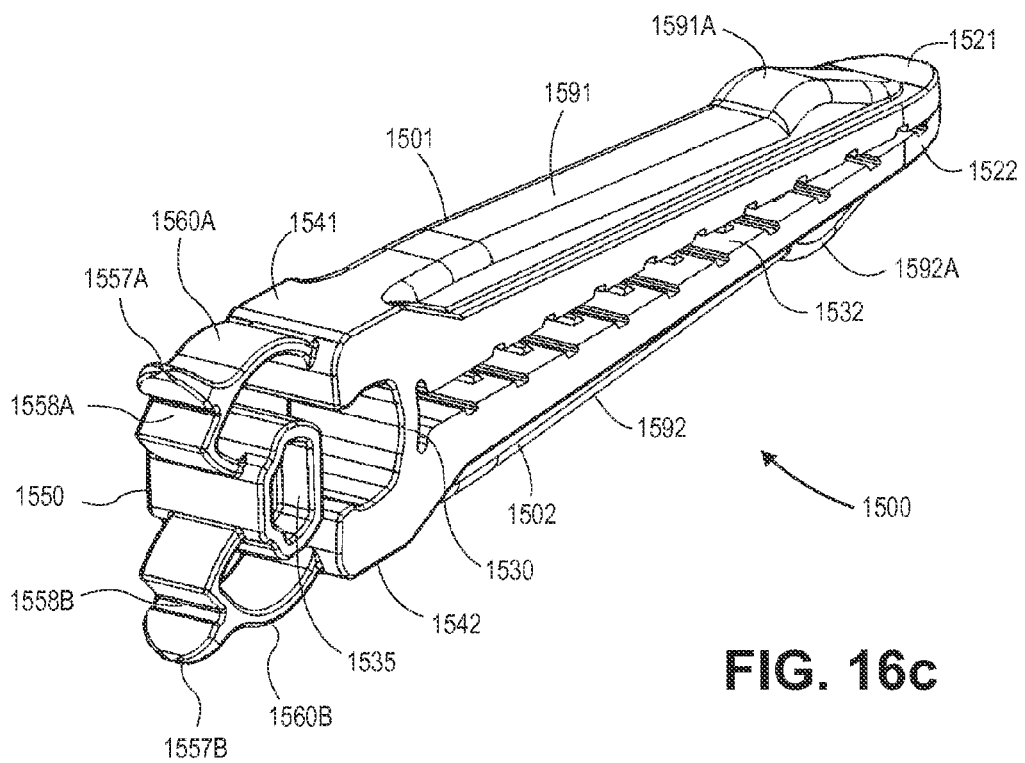

In the embodiment shown in FIG. 16a, and as best shown in FIG. 16b or 18b, the clip 1500 comprises structural reinforcing flanges 1591 and 1592 extending longitudinally across respective outer surfaces of each of the first and second legs 1501 and 1502 which are on opposite sides to the inner clamping surfaces 1531, 1532 of each respective leg, the flange 1591 of the first leg 1501 extending from the first jaw structure 1541 to the distal end portion 1521 of the first leg 1501, the flange 1592 of the second leg 1502 extending from the second jaw structure 1542 to the distal end portion 1522 of the second leg 1502. Each of the flanges 1591, 1592 can further define a transverse protrusion 1591a, 1592a, respectively, extending transversely outwards away from the longitudinal axis L proximate the distal end portions of the legs, which can aid in the actuation of the clip legs during movement or application through an applier tool.

It is further generally understood that one or more features of any one or more of the clips disclosed herein may be interchanged or added or omitted as further distinct embodiments of the present invention.

The various embodiments of the surgical clips of the present invention are preferably made of one or more polymer materials, such as, by example, acetyl homopolymer, but could also be made of a variety of other materials, including one or more metals, or a combination of metal and polymer or plastic. In selecting the material(s) used, the radiopacity of the clip can be "tuned" to a desirable level, or can be tuned to be radiopaque.

The clamping surfaces of the clips of the present invention, as disclosed in the embodiments discussed herein, may have clamping surfaces with a concave arc designed in place, such that the proximal and distal ends of the clamping surfaces are in close proximity, while the centers are further apart. The arcing surface will provide a more even distribution of force along the clamping surface when the clip is in locked closed condition.

The various embodiments of surgical clips of the present invention are an improvement over the known polymeric surgical ligation clips, as well as standard metal clips. Among the resulting advantages of the surgical clip of the invention as disclosed herein are: the ability to deliver a larger clip through a smaller endoscopic instrument; the ability to place a clip on a vessel just like a prior art malleable and deformable metal clip, with no need for added dissection or cleaning around the vessel, but with greater retention force than metal clips, which results in a reduced risk of clips slipping off the vessels. The greater clip locking stability and clip retention force is accomplished by the locking feature applying an active biasing or clamping force as discussed above, versus the passive clamping action created by plastic deformation of malleable metal clips.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention. All ranges cited herein specifically incorporate all values and sub-ranges within the cited range.

What is claimed is:

1. A surgical ligation clip, defining a longitudinal axis and comprising:

first and second legs each extending along the longitudinal axis and having proximal and distal end portions with respect to said longitudinal axis, a clip hinge joining the first and second legs at a point on their respective proximal end portions, the first and second legs each having inner clamping surfaces between the clip hinge and the distal end portions of said first and second legs, the clamping surfaces being substantially apposed when the clip is in a fully closed position, a first jaw structure on the first leg extending proximal to the clip hinge, the first jaw structure having a first curved inner surface extending proximally from the clip hinge and facing the longitudinal axis and being substantially concave viewed from said axis, a second jaw structure on the second leg extending proximal to the clip hinge, the second jaw structure having a second curved inner surface extending proximally from the clip hinge and facing the longitudinal axis and being substantially concave viewed from said axis, and a buttress body extending from and connected to both the first jaw structure and the second jaw structure by a first living hinge and second living hinge, respectively extending from said first jaw structure and second jaw structure, the buttress body having an outer surface, the first and second jaw structures being spaced from the longitudinal axis on opposite sides thereof and defining a locking space therebetween, the buttress body being moveable into the locking space such that at least first and second curved planar segment abutment portions of the outer surface of the buttress body each abuts against the substantially concave curved inner surfaces of the first and second jaw structures to bias the clip in a closed position, wherein the buttress body forms a substantially cylindrical or generalized cylindrical body spanning laterally on a proximal end of the clip, and the locking space is a socket space and a volume subtended by the buttress body can occupy substantially all of said socket space, and wherein when said buttress body is disposed in said locking space, abutment of the buttress body against the respective substantially concave curved inner surface of each of the first jaw structure and second jaw structure creates moments acting about the clip hinge directly on the first and second jaw structures, which moments directly act on the first and second legs to urge said legs closed and supply a clamping force between said legs.

2. The surgical clip of claim 1, wherein the first and second curved planar segment abutment portions of the outer surface of the buttress body each form a convex outer surface when facing the longitudinal axis and which are complementary to the substantially concave curved inner surfaces of the first and second jaw structures.

3. The surgical clip of claim 2, wherein the convex first and second curved planar segment abutment portions of the outer surface of the buttress body are symmetrical about the longitudinal axis and the substantially concave curved inner surfaces of the first and second jaw structures are symmetric about the longitudinal axis.

4. The surgical clip of claim 3, wherein each of the curved inner surfaces of the first and second jaw structures forms a lip at a proximal end of each jaw structure extending transversely inwardly towards the longitudinal axis to grip against the proximal ends of each of the first and second curved planar segment abutment portions of the outer surface of the buttress body when said body is moved in the locking space.

5. The surgical clip of claim 3, wherein a vector from a centerpoint lateral axis of the buttress body through a midpoint lateral span of either of the convex first and second curved planar segment abutment portions of the outer surface of the buttress body forms an angle of about 70 to 75 degrees from the longitudinal axis.

6. The surgical clip of claim 1, wherein a transverse cross-section of the buttress body is substantially hexagonal having at least a plurality of curved side segments.

7. The clip of claim 1, wherein the buttress body defines at least one recess extending laterally inwards into a lateral side of said buttress body.

8. The surgical clip of claim 1, wherein each of the inner clamping surfaces define a plurality of teeth and grooves, the teeth and grooves on the first leg being aligned complementary to grooves and teeth, respectively, of the second leg.

9. The surgical clip of claim 1, wherein each of the inner clamping surfaces further defines a concave radius of curvature when facing transversely away from the longitudinal axis towards said inner clamping surface.

10. The surgical clip of claim 1, further comprising flanges extending longitudinally across respective outer surfaces of each of the first and second legs which are on opposite sides to the inner clamping surfaces of each respective leg, the flange of the first leg extending from the first jaw structure to the distal end portion of the first leg, the flange of the second leg extending from the second jaw structure to the distal end portion of the second leg.

11. The surgical clip of claim 10, wherein each of the flanges defines a transverse protrusion extending transversely outwards away from the longitudinal axis proximate the distal end portions of the legs.

* * * * *